United States Patent [19]
Esaki et al.

[11] Patent Number: 5,216,244
[45] Date of Patent: Jun. 1, 1993

[54] ACCESSORY AND CRYSTALLINE ELEMENT FOR ATTENUATED TOTAL REFLECTION INFRARED SPECTROSCOPY

[75] Inventors: Yasuo Esaki; Kyoko Yokokawa; Toshimi Araga, all of Aichi, Japan

[73] Assignee: Kabushiki Kaisha Toyota Chuo Kenkyusho, Aichi, Japan

[21] Appl. No.: 726,332

[22] Filed: Jul. 5, 1991

[30] Foreign Application Priority Data

Jul. 6, 1990 [JP] Japan .................................. 2-180281
Nov. 30, 1990 [JP] Japan ............................. 2-130567[U]
Dec. 26, 1990 [JP] Japan .................................. 2-418424

[51] Int. Cl.$^5$ ...................... G01N 21/17; G01N 21/55
[52] U.S. Cl. .................................... 250/339; 250/341; 250/347; 250/359.1; 250/360.1; 356/244
[58] Field of Search ........................ 356/244, 300, 346; 250/339, 340, 341, 347, 353, 359.1, 360.1

[56] References Cited

U.S. PATENT DOCUMENTS

| | | | |
|---|---|---|---|
| 3,240,111 | 3/1966 | Sherman | 356/300 |
| 3,490,847 | 1/1970 | Berz et al. | 356/244 |
| 3,902,807 | 9/1975 | Fleming et al. | 250/343 X |
| 4,602,869 | 7/1986 | Harrick | 356/244 |
| 4,681,451 | 7/1987 | Guerra et al. | 356/373 |
| 4,746,179 | 5/1988 | Dahne et al. | 356/133 X |
| 9,889,427 | 12/1989 | Van Veen et al. | 356/445 |

OTHER PUBLICATIONS

Martin, "Infrared Instrumentation and Techniques", Elsevier Publishing Co., QD 95 M38, 1966, pp. 155–169.

Primary Examiner—Constantine Hannaher
Assistant Examiner—Edward J. Glick
Attorney, Agent, or Firm—Oblon, Spivak, McClelland, Maier & Neustadt

[57] ABSTRACT

The accessary for attenuated total reflection infrared spectroscopy comprises a condenser mirror, a crystalline element, a sample-supporting portion holding the crystalline element, an objective mirror, and a slit. The crystalline element has an incident surface, a totally reflecting surface, and an exit surface. A sample to be investigated is contacted with the totally reflecting surface The focused point of the infrared radiation from the condenser mirror is at the point of measurement on the totally reflecting surface of the crystalline element The focus of the objective mirror can be brought to the point of measurement on the sample surface. A point analysis, line analysis, or area surface on the order of 10 μm can be made while observing the sample with the naked eye with the objective mirror. The invention further includes improvements in the mechanism for automatically adjusting the focus of the objective mirror when the measurement point is changed. Another improvement is that the crystalline element has the reflecting surfaces oriented individually so that the optical axis of the incident radiation rays can agree with the optical axis of the outgoing radiation rays. A further improvement is that a scale for determining a measurement point is engraved on the totally reflecting surface of the crystalline element.

17 Claims, 21 Drawing Sheets

FIG. 6
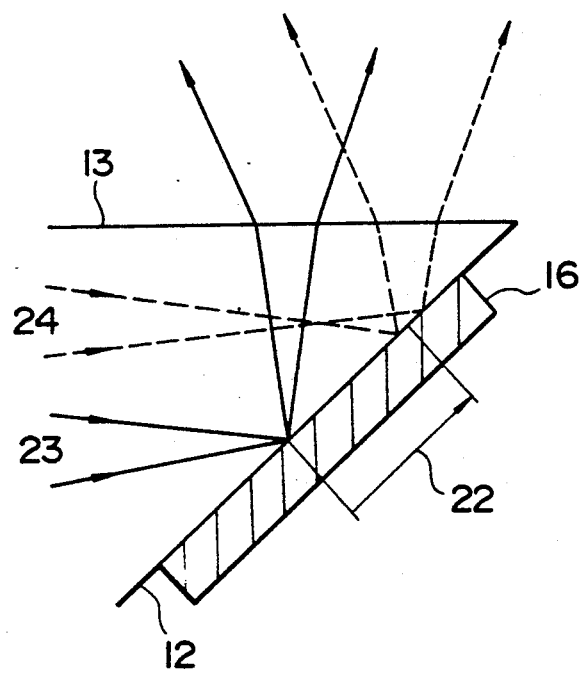
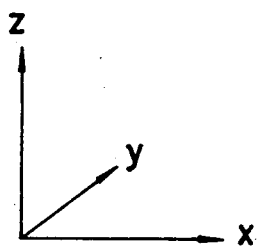

ACCESSORY AND CRYSTALLINE ELEMENT FOR ATTENUATED TOTAL REFLECTION INFRARED SPECTROSCOPY

BACKGROUND OF THE INVENTION

1. Field of the Invention

The present invention relates to an accessory for attenuated total reflection (ATR) infrared (IR) spectroscopy for making a point analysis, line analysis, or area analysis of the surface of a sample, using infrared radiation. The invention also relates to a crystalline element used for ATR IR spectroscopy.

2. Description of the Related Art

Where a crystalline element of a higher relative index of refraction (i.e., the index of refraction of a material divided by the index of refraction of air; hereinafter referred to as the index of refraction) is brought into intimate contact with a sample of a lower index of refraction under examination, if infrared radiation is made to enter the interface between the crystalline element and the sample at an angle exceeding the critical angle, then the radiation penetrates to a certain depth into the sample and then totally reflects. Therefore, if the sample absorbs infrared radiation, then the intensity of the totally reflected light decreases, i.e., the totally reflected light attenuates, according to the intensity of the absorption. An ATR IR spectrum intrinsic to the sample is obtained by detecting the totally reflected light. An accessory for measuring the absorption of totally reflected infrared radiation analyzes such a spectrum to obtain information about the chemical composition of the surface layer of a sample having a thickness of several microns. This kind of accessory is widely used to make a surface analysis of polymeric materials of relatively low indices of refraction, such as rubber, films, and plastics.

A typical example of the prior art accessory for ATR IR measurements is shown in FIG. 23. This accessory utilizes multiple total reflections and includes a condenser mirror 1 which converges infrared radiation onto the incident surface 3 of a crystalline element 2 where total reflection takes place. The radiation enters the crystalline element 2 and totally reflects many times inside it. A sample 5 to be investigated is placed in intimate contact with the totally reflecting surface 4 of the crystalline element 2. During the multiple total reflections inside the crystalline element, the infrared radiation is totally reflected a plurality of times at the interface between the sample 5 and the crystalline element 2 to improve the sensitivity of the accessory in making the surface analysis. Infrared radiation exiting from the exit surface 6 is directed to a detector (not shown) via an objective mirror 7. The cross section of the conventional crystalline element assumes various forms including parallelogram and trapezoid as shown in FIG. 22 (1)–(3).

In recent years, strict demands have been made on micron order analyses of samples. For example, it has been required to make a surface analysis of a microscopic region having dimensions on the order of 10 microns on the surface of a sample.

In the above-described accessory performing ATR IR measurements using multiple total reflections, the infrared radiation is focused onto the incident surface 3 of the crystal. Therefore, it is inevitable that the infrared radiation is dispersed inside the crystal. Also, it is difficult to efficiently focus the infrared radiation onto the sample. For these and other reasons, it is difficult to enhance the efficiency of utilization of the quantity of light in the microscopic area under investigation. Therefore, the accessory cannot analyze areas smaller than an area having dimensions of the order of 100 microns. Even if the infrared radiation emanating only from a sample surface portion having dimensions on the order of 10 microns is selected using a slit, satisfactory ATR IR spectra cannot be obtained because of insufficiency of the intensity of the infrared radiation from the sample surface portion of interest, the insufficiency being caused by insufficient efficiency of utilization of the quantity of light. Hence it is impossible to analyze this sample surface portion.

The above-described demand for microscopic analysis may require that a line analysis on the order of 10 microns be made. The prior art accessory for ATR IR spectroscopy cannot satisfy this requirement because of the limited ability of analysis as mentioned above. In addition, the accessory is intrinsically unsuitable for the above-described requirement for making an analysis along a line, because the multiple total reflection method involves taking the average of values derived from plural sample surface portions where the plural total reflections of infrared radiation take place.

Another requirement is an area analysis on the order of $10\mu$. The prior art accessory for ATR IR measurements cannot fulfill this requirement for the same reason as in the case in which a sample surface is analyzed along a line.

In the prior art accessory utilizing multiple total reflections for making ATR IR measurements, it is customary to bring the focus of the objective mirror onto the exit surface of the crystalline element to obtain the maximum amount of infrared radiation. Thus it is impossible to make a point analysis, line analysis, and especially area analysis of the specific sample portion. Also, it is impossible to visually observe a certain point of measurement via the objective mirror, because the focus is not on the measurement point. In this way, if the function of visual observation via the objective mirror is added in the prior art, it has been useless for microscopic analysis.

With the prior art crystalline element for producing total reflections, the optical axis of the outgoing rays deviates from the optical axis of the incident rays as indicated by the broken lines in FIG. 22. This makes it impossible to dispose the condenser mirror 1 and the objective mirror 7 on the same axis, as shown in FIG. 23. Therefore, the prior art crystal cannot be applied to the conventional infrared microscope because it has condenser optics where the condenser mirror and the objective mirror are arranged on the same axis.

If this microscopic measurement by ATR IR spectroscopy is made, it is difficult to visually identify a point of interest on the sample surface. It is because the sample does not sufficiently adhere to the crystal and because the visible light penetrates less deep into the sample than infrared radiation on total reflection. In order to solve the foregoing problem, an index for locating the microscopic point of measurement is needed.

SUMMARY OF THE INVENTION

A first aspect of the invention lies in an accessory which is used for attenuated total reflection (ATR) infrared spectroscopy and which comprises a condenser mirror, a crystalline element for total reflection, a slit, and an objective mirror, the optical path length of the accessory being so set that the focused point of the infrared radiation is located on the totally reflecting surface of the crystalline element.

A second aspect of the invention lies in a crystalline element having an incident surface on which infrared radiation is incident, at least three reflecting surfaces including a totally reflecting surface, and an exit surface from which the infrared radiation exits. A sample to be investigated is contacted with the totally reflecting surface, for performing ATR IR measurements. The reflecting surfaces are so oriented that the optical axis of the incident radiation agrees with the optical axis of the outgoing radiation.

A third aspect of the invention lies in a crystalline element having at least one totally reflecting surface with which a sample to be investigated is contacted for performing ATR IR measurements and a scale engraved on the totally reflecting surface deeper than the surface roughness of this totally reflecting surface.

Other objects and features of the invention will appear in the course of the description thereof which follows.

BRIEF DESCRIPTION OF THE DRAWINGS

FIG. 1 (*c*) and (*d*) are side elevations of crystalline elements according to the invention;

FIG. 3(*b*) is a side elevation of the accessory equipped with an optical system shown in FIG. 3(a);

FIG. 6 is a diagram illustrating deviation of the focused point when a crystalline element is moved in the x-direction;

DETAILED DESCRIPTION OF THE INVENTION

Figure 1A:
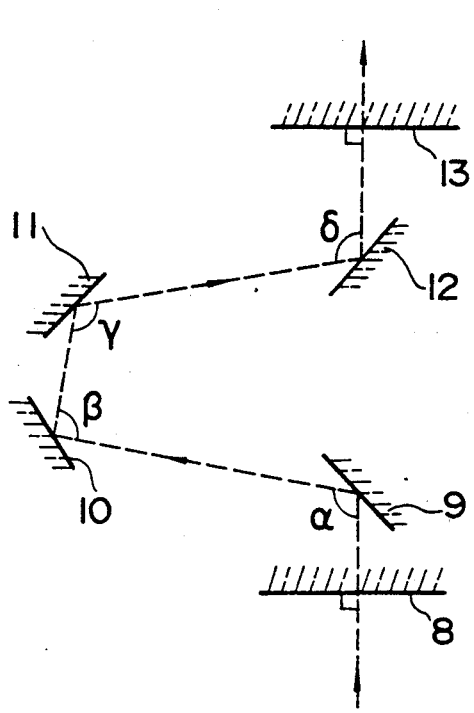
FIG. 1 (*a*) and (*b*) are diagrams illustrating the angle of reflection for determining the shape of a crystalline element according to the invention.

The first aspect of the invention is an accessory for attenuated total reflection (ATR) infrared (IR) spectroscopy, the accessory comprising: a condenser mirror for converging infrared radiation; a sample-holding portion holding a sample to be investigated; a crystalline element placed on the sample-holding portion and having an incident surface on which infrared radiation coming from the condenser mirror falls, a totally reflecting surface with which the sample is contacted and which permits a single (not multiple) total reflection of infrared radiation therefrom, and an exit surface through which the infrared radiation finally exits from the crystalline element; a slit for selectively passing the infrared radiation exiting from the exit surface; and an objective mirror which is disposed opposite to the exit surface of the crystalline element and which can be focused to the point of measurement of the sample fixed to the totally reflecting surface The optical path length of the accessory is so set that the converged point of the infrared radiation lies on the totally reflecting surface of the crystalline element.

In the first aspect, the infrared radiation converged by the condenser mirror is made to enter the crystalline element from its incident surface. The incident rays are focused onto the totally reflecting surface and reflected totally only once. Then, only the outgoing rays totally reflected from the point of measurement on the sample surface are extracted from the infrared radiation exiting from the exit surface by the slit. In this way, a spectrum of the absorption of the infrared radiation totally reflected from the sample surface under examination is obtained. In the novel method, it is rational to bring the focus of the objective mirror to the point at which a maximum amount of the infrared radiation is obtained, i.e., the point of measurement on the sample surface.

This objective mirror allows one to visually observe the sample surface at the same time without making any preparations.

Of the infrared radiation leaving the exit surface, only the outgoing rays totally reflected from the point of measurement having dimensions on the order of 10 microns are extracted by the slit. In spite of this, the infrared radiation is dispersed only a little inside the Crystalline element, since multiple total reflections do not occur on the sample surface. Also, the infrared radiation is focused onto the totally reflecting surface. For these and other reasons, the efficiency of utilization of the quantity of light per unit area of the sample surface is high and so the absorption of the totally reflected infrared radiation can be efficiently measured even on the present technical level of the infrared detector. In this way, in the first aspect, microscopic portions of the sample surface having dimensions on the order of 10 microns can be analyzed while visually observing the surface via the objective mirror.

In the first aspect, the crystalline element for the accessory for ATR IR spectroscopy can be a pillar having an incident surface, a totally reflecting surface, and an exit surface. These surfaces are plane surfaces parallel to the axis of the pillar which is at right angles to the optical axis of the outgoing rays. The sample-holding portion has a drive mechanism capable of translating the crystalline element at least along the axis of the pillar.

In this case, the crystalline element with which a sample to be investigated is contacted is translated along the axis of the pillar to make a line analysis on the order of 10 microns in the direction of movement. At this time, neither the optical path length for the infrared radiation inside the crystalline element nor the relative position of the totally reflecting surface of the crystalline element changes at all. Therefore, the focused point of the infrared radiation is maintained on the totally reflecting surface of the crystalline element. That is, accurate line analysis is accomplished because the condition for total reflection is constant even if the crystalline element is translated along the axis of the pillar. It is desired to visually observe the sample surface via the objective mirror simultaneously with the line analysis. In this way, a line analysis on the order of 10 microns on the surface of the sample can be carried out while visually observing the sample via the objective mirror by performing a simple operation, i.e., the crystalline element which bears the sample under investigation is translated along the axis of the pillar.

In the first aspect, the crystalline element for the accessory for ATR IR spectroscopy is the pillar having the incident surface, the totally reflecting surface, and the exit surfaces which are plane surfaces parallel to the axis of the pillar. The axis of the pillar is at right angles to the optical axis of the outgoing rays. The sample-holding portion has a drive mechanism capable of translating the crystalline element at will in three dimensions. The drive mechanism is equipped with a control system comprising: a calculating means for calculating the forecasted traveling length of the crystalline element to adjust the focus of the objective mirror at a new measurement point on the totally reflecting surface when the crystalline element is translated not along the axis of the pillar; and a control means providing control of the operation of the drive mechanism according to the results of the calculations.

In this case, if the crystalline element which bears the sample to be investigated is translated along the axis of the pillar, then the same result arises as in the above-described result obtained by line analysis. If the translation of the crystalline element includes movement perpendicular to the axis of the pillar, then the focus will not be just at the point of measurement, depending on the numerical apertures of the objective and condenser mirrors and on the refractive index of the crystalline element. The control system which is informed of the intended traveling distance on the sample surface calculates the amount of traveling the crystal along the optical axis of the outgoing rays to adjust the focus of the objective mirror at the new measurement point, and operates the drive mechanism according to the results of the calculations to move the crystalline element in such a way that the focus will not deviate from the point of measurement. This enables automatic area analysis of the sample surface. In making an area analysis, the focus of the objective mirror is kept coincident with the point of point of measurement. Consequently, it is desired to visually observe the sample surface via the objective mirror simultaneously. In this way, a line analysis or area analysis of each microscopic portion having dimensions on the order of 10 microns on the sample surface can be made while visually observing the sample surface via the objective mirror, because the focus of the mirror is kept coincident with the point of measurement on the surface of the sample to be investigated.

The second aspect of the invention lies in a crystalline element placed on a sample-holding portion holding a sample to be investigated in an accessory for ATR IR spectroscopy, the crystalline element comprising an incident surface on which infrared radiation coming from a condenser mirror falls, a totally reflecting surface bearing the sample to totally reflect the infrared radiation, at least three reflecting surfaces including the totally reflecting surface and acting to alter the direction of the incident rays, and an exit surface through which the infrared radiation finally exits from the crystalline element. The reflecting surfaces are so oriented that the optical axis of the incident rays agrees with the optical axis of the outgoing rays.

In the second aspect, the incident infrared radiation is reflected at least three times by the at least three reflecting surfaces which have given angular relations to each other. The at least three reflecting surfaces include the totally reflecting surface which bears the sample to be investigated. In this way, the radiation exits from the crystalline element along the same axis as the axis of the incident radiation. Therefore, it is assured that the optical axis of the outgoing rays agrees with the optical axis of the incident rays. Hence an accessory measuring the absorption of totally reflected infrared radiation can be fabricated using the conventionally often used infrared microscope having condenser optics where the condenser mirror and the objective mirror are arranged on the same axis. The present invention realizes ATR IR spectroscopy without modifying the structure of the conventional microscope.

In this second aspect, the crystalline element can be used to produce total reflections for the first aspect of the accessory for ATR IR spectroscopy. In this case, the advantages of the first aspect and the advantages of the second aspect can be obtained simultaneously.

The third aspect of the invention is a crystalline element having at least one totally reflecting surface which bears a sample for ATR IR measurements and a scale engraved on the totally reflecting surface deeper than the surface roughness of this totally reflecting surface. Light enters this crystalline element and reaches the totally reflecting surface. When the light hits the scale engraved on the totally reflecting surface, the light is scattered. This permits the scale to be checked with the totally reflected light. This phenomenon takes place irrespective of the kind of the incident radiation. It is no wonder that this phenomenon occurs where the incident radiation is visible light and the scale can be visually observed.

Figure 21:
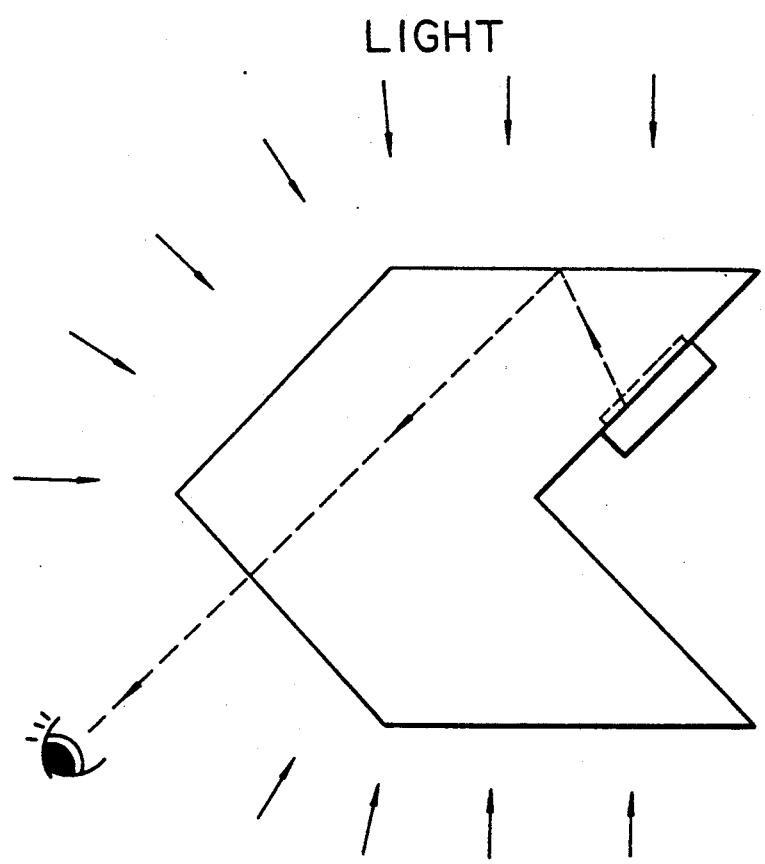
FIG. 21 is a schematic diagram showing the path of visible light to an eye for determining the positional relation between a sample under investigation and a scale using an ordinary optical microscope.
Figure 22:
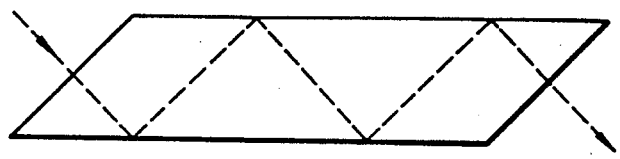
FIG. 22 (1)–(3) are views showing conventional crystalline elements and their optical paths.
Figure 22:
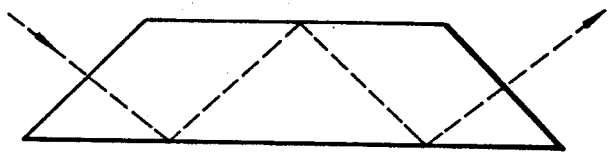
Figure 22:
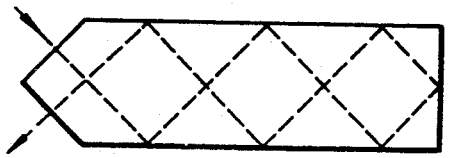
Figure 23:
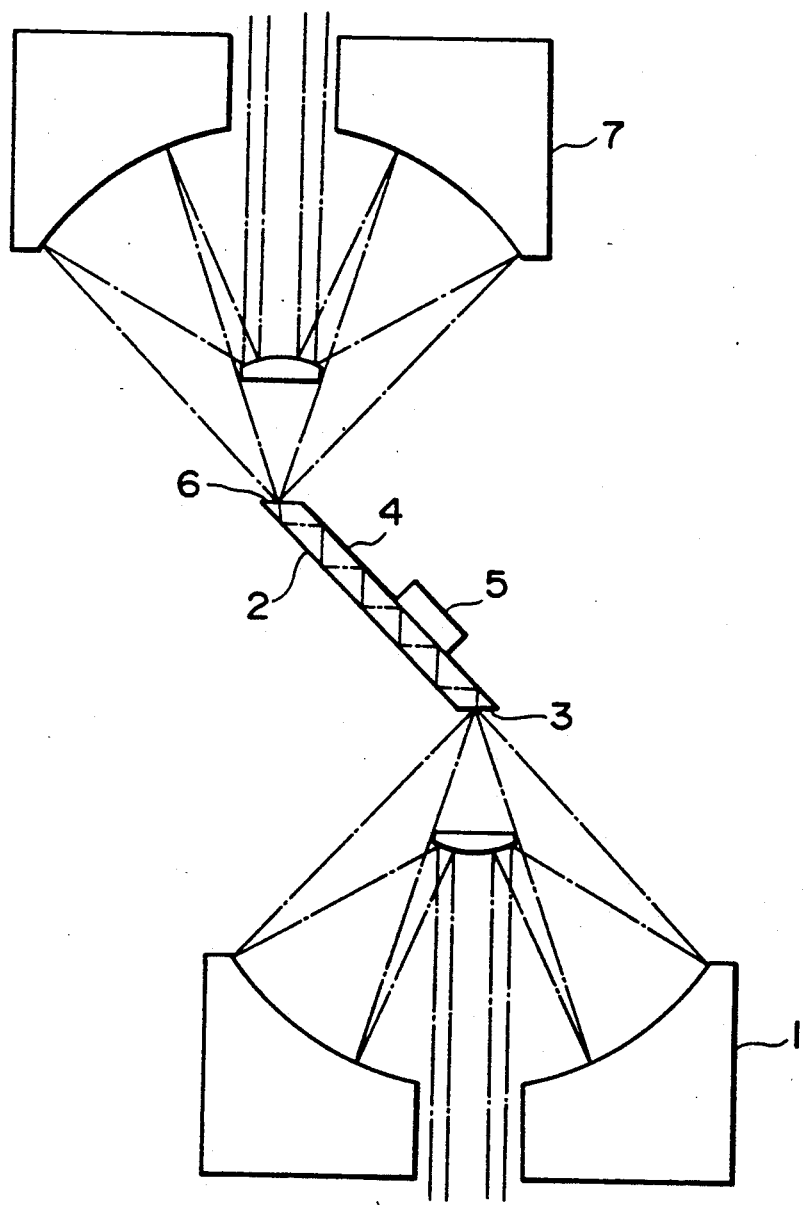
FIG. 23 is a vertical cross section of an optical system, for illustrating the prior art method of performing ATR IR measurements.

The sample for ATR IR measurements is brought into intimate contact with the scaled, totally reflecting surface of the novel crystalline element. Visible light is directed to it from the surroundings under an ordinary optical microscope. Under this condition, the positional relation between the scale and the point of measurement on the sample surface can be forecasted (see FIG. 21). In FIG. 21, both scale and sample surface can be observed, since ordinary reflected light is employed. The sample is moved onto an accessory for ATR IR spectroscopy while the sample is kept in intimate contact with the surface of the crystalline element. The totally reflected light is visible radiation, and an observation is made. The point of measurement on the sample surface can be quickly and accurately determined with the precision corresponding to the intervals between the successive marks of the scale. At this time, observation of the sample surface may be hindered because of small penetrating depth of visible radiation on the totally reflecting surface, but the scale can be clearly seen. Accordingly, the point of measurement on the sample surface can be quickly and accurately determined, based on the scale and also on the forecasted relative positional relation between the scale and the sample. Various embodiments of the invention are hereinafter described.

EMBODIMENTS

Figure 1B:
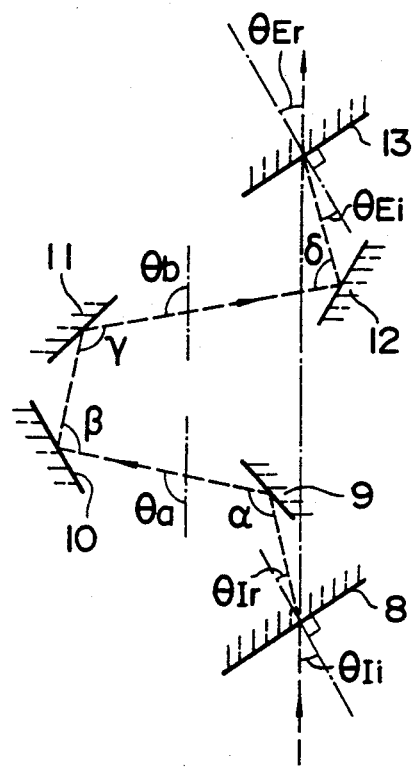
Figure 1C:
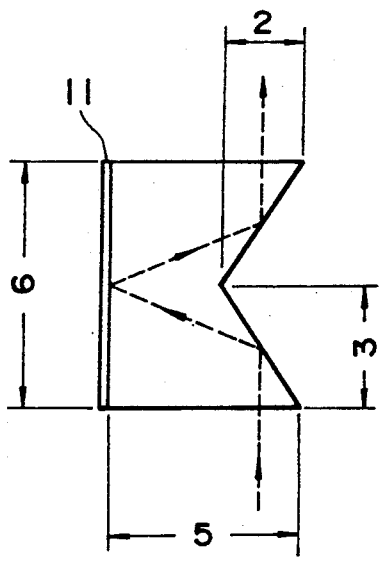
Figure 1D:
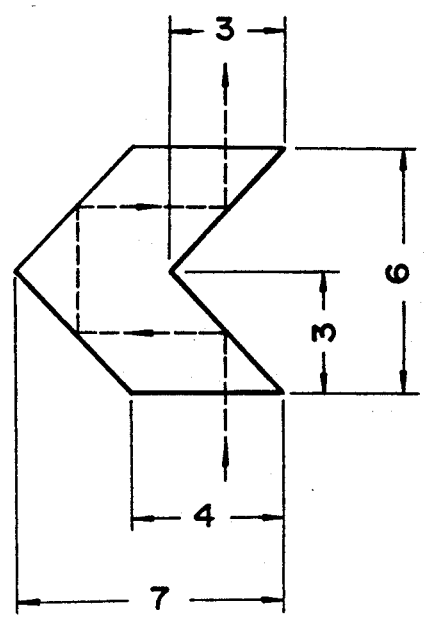

FIG. 1(a)–(d) show embodiments of the second aspect described above. FIG. 1(c) shows a pillar-shaped crystalline element which assumes the form of a pentagon as viewed along the axis of the pillar. The geometrical path that infrared radiation follows is indicated by the broken lines including arrows. This crystalline element has an incident surface, three reflecting surfaces, and an exit surface. One of the three reflecting surfaces is a totally reflecting surface with which a sample to be investigated is contacted. A film 11 processed so as to reflect light is formed on one of the reflecting surfaces. FIG. 1(d) shows another pillar-shaped crystalline element which takes the form of a hexagon as viewed along the axis of the pillar. The direction of propagation of infrared radiation is indicated by the arrows attached to the broken lines. This crystalline element has an incident surface, four reflecting surfaces, and an exit surface. One of the four reflecting surfaces is a totally reflecting surface against which a sample to be investigated is caused to abut. FIG. 1(d) shows a ratio of 4/6 for the width of the incident surface of the element to the length or distance between the incident and exit surfaces. However, the ratio could be as small as ½ without incurring plural total reflections from the totally reflecting surface in contact with the sample. The numerals contained in FIG. 1(c) and (d) show ratios of the lengths of the sides of the crystalline elements. In each of FIG. 1 (c) and (d), the incident surface, the reflecting surfaces, and the exit surface are plane surfaces parallel to the axis of the pillar. In each of these crystalline elements, the incident light is reflected three or four times inside the element as indicated by the arrows showing the direction of the geometrical path. The optical axis of the outgoing rays is coincident with the optical axis of the incident rays. In the geometries of FIG. 1(c) and (d), which of the reflecting surfaces is selected as the totally reflecting surface bearing the sample is determined at will, depending on the relation to the whole structure of the accessory for ATR IR spectroscopy.

We next give a general formula applied to the case in which an arbitrarily shaped crystal is placed in an optical system where the incident rays and the outgoing rays are on the same axis. In this crystal, infrared radiation is reflected four times. FIG. 1(a) shows the geometrical path in the optical system in which the incident surface 8 and the exit surface 13 of the crystalline element are parallel to each other and vertical to the optical axis of the incident rays. Reflecting surfaces 9, 10, 11, and 12 exist inside the crystal and are located in this order from the side of the incident surface. Let $\alpha$, $\beta$, $\gamma$, $\delta$ be the angles formed between the incident radiation and the outgoing radiation at these reflecting surfaces, respectively. The shape of the crystal is determined by the four reflecting surfaces inside it, the incident surface, and the exit surface. These surfaces satisfy the following equation $$\alpha + \delta = \beta + \gamma \tag{1}$$

where at least one of the angles $\alpha$, $\beta$, $\gamma$, $\delta$ is at least twice as large as the critical angle and fulfills the condition for total reflection.

In the geometry shown in FIG. 1(b), the incident surface 8 and the exit surface 13 of the crystalline element are not parallel to each other and tilted at arbitrary angles towards the optical axis of the incident radiation. In this case, the left side of equation (1) is compensated for by the terms of the angles of incidence and the angles of refraction at the incident and ext surfaces. As a result, equation (2) is derived. That is, in this case, the shape of the crystal is determined by the four reflecting surfaces satisfying equation (2) provided that the angles of incidence and departure at the incident and exit surfaces, and the refractive index of the crystalline element are given.

$$(\alpha \pm \theta_I) + (\delta \pm \theta_E) = \beta + \gamma \tag{2}$$

where $\theta_I = \theta_{Ii} - \theta_{Ir}$ $\theta_E = \theta_{Er} - \theta_{Ei}$ where $\theta_{Ii}$ is the incident angle at the incident surface 8, $\theta_{Ir}$ is the angle of refraction at the incident surface 8, $\theta_{Er}$ is the angle of refraction at the exit surface 13, and $\theta_{Ei}$ is the angle of incidence at the exit surface 13.

The terms in the parentheses of the left side of equation (2) are $\alpha - \theta_I$ if $\alpha > \theta_a$ $\alpha + \theta_I$ if $\alpha < \theta_a$ $\delta - \theta_E$ if $\delta > \theta_b$ $\delta + \theta_E$ if $\delta < \theta_b$ where $\theta_a$ is the angle formed between the optical axis of the first reflecting light and the incident and exit axes, and $\theta_b$ is the angle formed between the optical axis of the third reflecting light and the incident and exit axes.

We have described thus far the case in which infrared radiation is reflected four times inside a crystalline material. The conditions under which the infrared radiation incident on the crystalline element exits from it on the same axis in a direction shifted by 360° with respect to the direction of incidence have also been theoretically described. A geometry in which radiation is reflected three times and a geometry in which radiation is reflected five or more times can similarly be found. Preferably, the incident and exit surfaces of the crystalline elements described above are vertical to the optical axis of the incident and outgoing radiation to suppress the reflection loss of the light at each surface. In addition, it is desired that these crystalline elements have simple shapes to facilitate obtaining total reflection conditions inside them and fabricating the elements. For this purpose, the angle formed between the incident surface of each crystalline element and the first reflecting surface and the angle made between the exit surface and the finally reflecting surface preferably lie between 30° and 60°. Furthermore, it is desired that the reflecting surfaces existing inside the crystalline element be made as few as possible.

The physics of the geometry in which infrared radiation is reflected four times and in which the finally reflecting surface is taken as the totally reflecting surface is now described by referring to FIG. 1(a). First, infrared radiation enters the crystalline element from the incident surface. The radiation is reflected at an angle of $\alpha/2$ by the first reflecting surface. The reflected light propagates through the crystalline element, and then it is reflected at an angle of $\beta/2$ by the second reflecting surface. Thereafter, the radiation is reflected at an angle of $\gamma/2$ by the third reflecting surface, and arrives at the finally reflecting surface. The infrared radiation incident on this finally reflecting surface meets the condition for total reflection, i.e., the incident angle lies between 30° and 60°. Therefore, the radiation is totally reflected at an angle of $\delta/2$. The optical axis of the totally reflected light is coincident with the optical axis of the incident light. The totally reflected light propagates in the direction shifted by 360° with respect to the direction of the incident radiation. At this time, the sample surface to be investigated is brought into intimate contact with the totally reflecting surface of the finally reflecting surface In consequence, the measurement of the absorption of the totally reflected infrared radiation is made possible.

The use of this embodiment of crystalline element assures that the infrared radiation leaving the crystalline element is on the same axis as the infrared radiation incident on the element. Therefore, an accessory for ATR IR spectroscopy can be fabricated using the conventionally often used infrared microscope having condenser optics where the condenser mirror and the objective mirror are arranged on the same axis without modifying the structure of this microscope.

Figure 2:
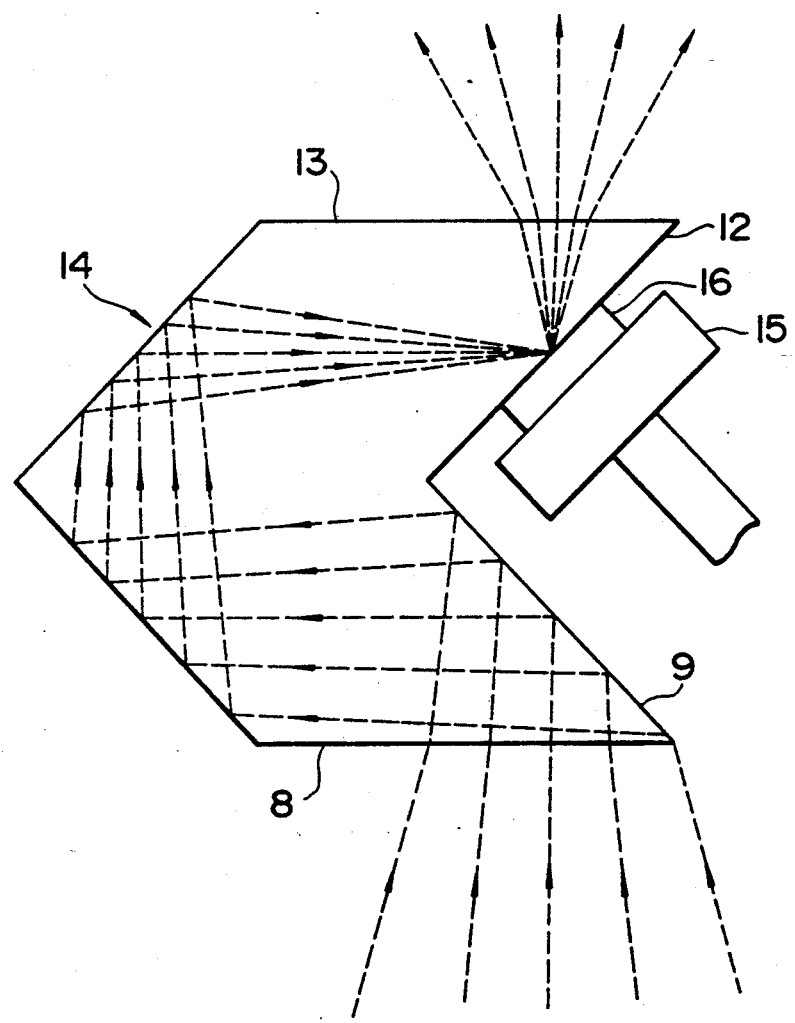
FIG. 2 is a side elevation of a crystalline element and associated components, for showing the condition in which the element is used.
Figure 3A:
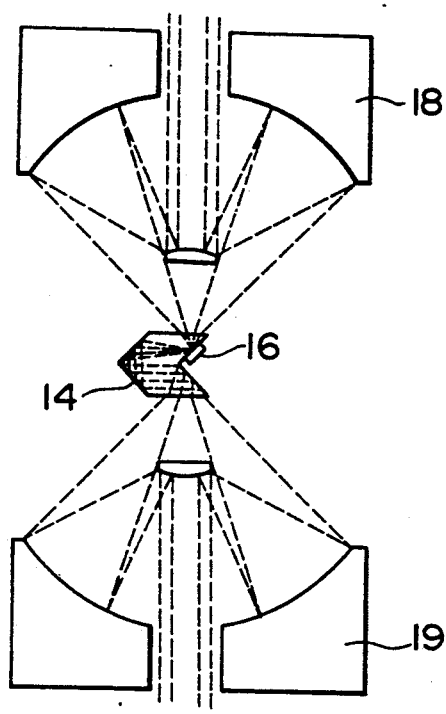
FIG. 3(*a*) is a vertical cross section of an optical system surrounding a crystalline element according to the invention.
Figure 3B:
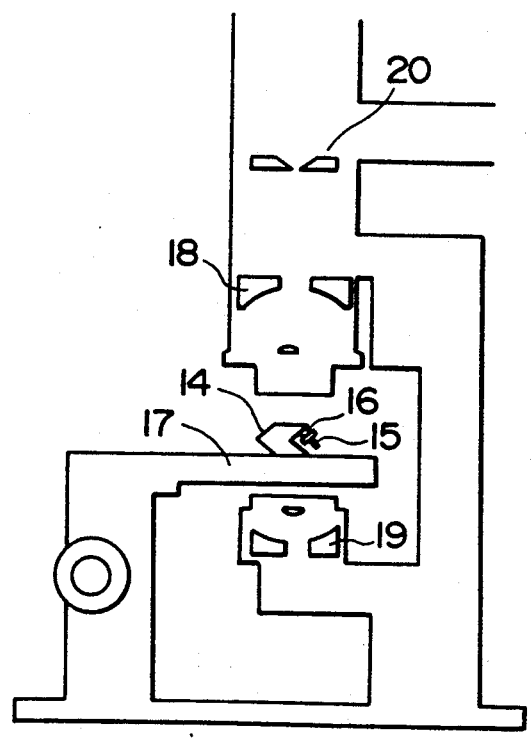

FIGS. 2 and 3 show an embodiment in which the crystalline element of the second aspect is applied to the first aspect. The crystalline element, indicated by 14, takes the aforementioned form shown in FIG. 1(d). That is, this assumes the form of a hexagonal pillar of substantially V-shaped cross section. The crystalline element 14 has an incident surface 8, a first reflecting surface 9, a finally reflecting surface 12, and an exit surface 13. A sample 16 under investigation is pressed against the finally reflecting surface 12 by a sample retainer 15.

The condition in which this crystalline element 14 is attached to a holder (not shown) and placed in an infrared microscope is shown in FIG. 3 (a) and (b). The crystalline element 14 attached to the holder is placed on a three-dimensional sample stage 17 that forms the sample-holding portion. An objective mirror 18 is mounted above the stage. A condenser mirror 19 is mounted below the stage. These mirrors 18 and 19 are located on the same axis. The objective mirror 18 is focused onto the finally reflecting surface 12. The lengths of the sides of the crystalline element 14 are adjusted in such a way that when it is attached to the infrared microscope, the focus of the condenser mirror agrees in position with the focus of the objective mirror. The sample stage 17 is either stationary or movable along the axis (or the depth in FIG. 3 (a) and (b)) of the pillar of the mounted crystalline element. Also, the sample stage can be moved at will in three dimensions. A movable slit 20 is attached to the infrared microscope to direct only the light reflected from the measured portion of the sample surface to the detector ancillary to the microscope. The radiation directed to the condenser mirror 19 is bipolar, i.e., it can be switched between infrared radiation and visible radiation by a movable reflecting mirror (not shown).

The sample 16 is brought into intimate contact with any one (the finally reflecting surface 12 in the present embodiment) of the totally reflecting surfaces of the crystalline element 14. The infrared radiation coming from the condenser mirror 19 is directed to the incident surface 8 The incident radiation is totally reflected inside the element 14 as shown in FIG. 2, converged onto the finally reflected surface 12, and penetrates to a certain depth into the sample. Then, the radiation totally reflects. The slit extracts only the infrared radiation emanating from the portion of interest 10 microns square from the totally reflected light. As a result, an ATR IR absorption spectrum is obtained from the microscopic portion 10 microns square on the sample 16. This spectrum is analyzed to analyze the microscopic portion on the sample surface.

In this embodiment, the sample stage 17 is moved to translate the crystalline element 14. ATR IR absorption spectra of the sample surface are obtained successively. In this way, a line analysis or area analysis of the sample surface can be made. Where a line analysis is made along the axis of the pillar forming the crystalline element 14, the focus of the objective mirror 18 will not deviate from the point of measurement. Where a line or area analysis is made in other directions, the focus of the objective mirror 18 will deviate from the point of measurement. To correct this deviation, the movement of the sample stage 17 is adjusted appropriately. During this movement for the adjustment, if necessary, the predetermined focus of the objective mirror 18 is also changed. The movement of the sample 16 for a line analysis or area analysis can be made more quickly and accurately by simultaneously observing the sample surface via the objective mirror 18. In this observation, as the adhesion of the sample 16 to the crystalline element 14 is improved and the absorption coefficient of the sample 16 for the visible radiation becomes higher, the observed image becomes divider.

An infrared absorption ATR spectrum can be obtained from a microscopic portion on the sample surface having dimensions on the order of 10 microns. The spectrum enables identification of the chemical composition of the surface layer and of chemical changes in the constituents. Also, aging and deterioration can be analyzed. Furthermore, the differences in chemical composition or chemical change among the portions on the sample surface can be known by a line analysis or area analysis. Development of commercial products or raw materials or improvements in them can be effectively promoted by analyzing the differences in aging or deterioration among the portions or the effects on them.

FIGS. 4 and 5 show second and third embodiments of the first aspect in which the condenser mirror and the objective mirror need not be arranged on the same axis. In these embodiments, objective mirror 18, condenser mirror 19, and sample stage 17 ar similar to the counterparts of the embodiment shown in FIGS. 2 and 3 and so they will not be described in detail below.

Figure 4A:
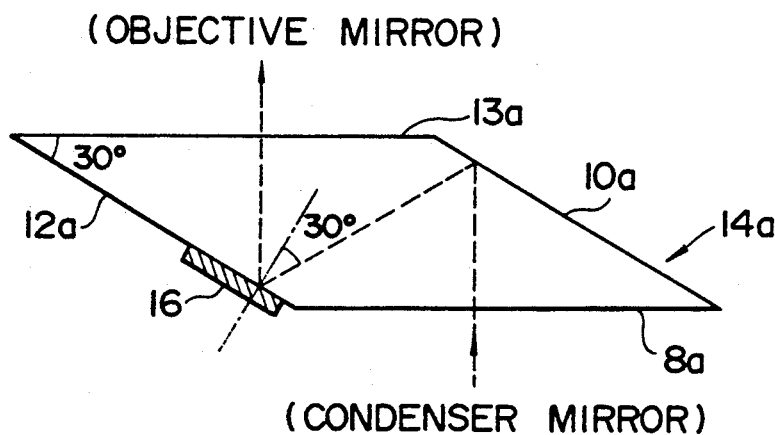
FIG. 4 (*a*), (*b*), (*c*) are views of other crystalline elements according to the invention.
Figure 4B:
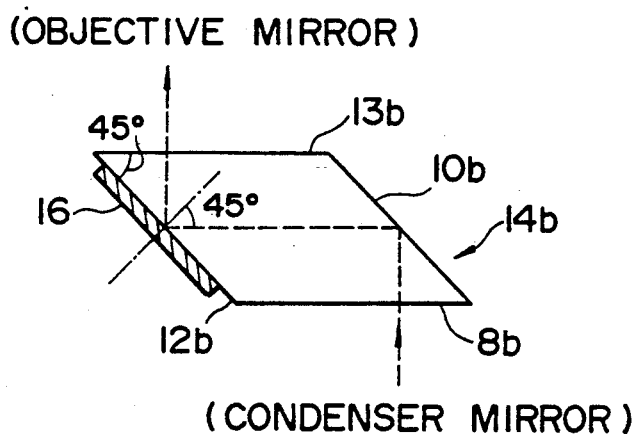
Figure 4C:
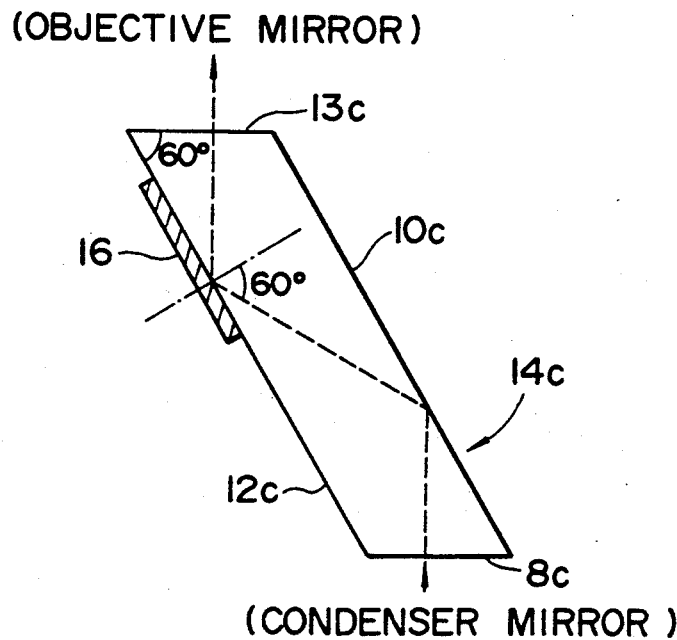

In the embodiments shown in FIG. 4(a)-(c), pillar-shaped crystal elements 14a, 14b, 14c, respectively, of parallelogrammatic cross section are used. Each crystalline element 14a, 14b, or 14c has one incident surface 8a, 8b, or 8c, one first reflecting surface 10a, 10b, or 10c, one finally reflecting surface 12a, 12b, or 12c, and one exit surface 13a, 13b, or 13c. The condenser mirror and the objective mirror (none of which are shown) are disposed in the geometrical paths indicated by the arrows. That is, they are arranged on the axes which are parallel to each other but spaced from each other. A sample 16 to be investigated can be contacted with the finally reflecting surface 12a, 12b, or 12c as shown for measurement. Also, it is possible that the sample 16 is contacted with the first reflecting surface 10a, 10b, or 10c. The internal acute angles of the parallelogram of the cross section of the crystalline element 14a, 14b, or 14c corresponds to the incident angle and the reflection angle at the reflecting surfaces 10a, 10b, or 10c and 12a, 12b, or 12c In the embodiment of FIG. 4(a), the acute angle is 30 degrees In the embodiment of FIG. 4(c), the acute angle is 60 degrees Although any desired angle between these two angles can be exploited as long as the condition for total reflection is met, angles in the neighborhood of 45° shown in FIG. 4(b) are preferable.

Figure 5A:
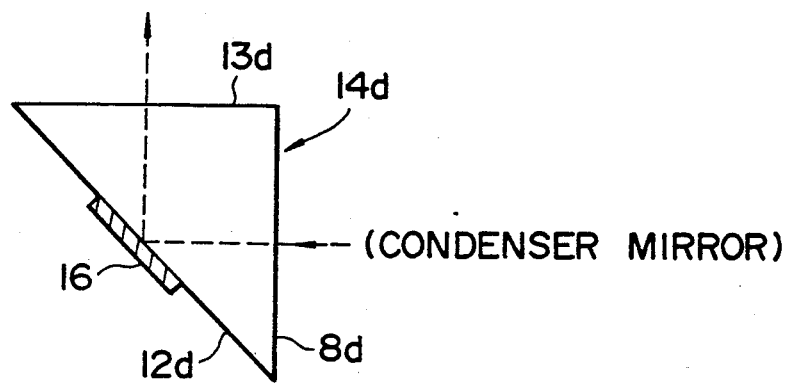
FIG. 5 (*a*) and (*b*) are views of a crystalline element which takes the form of a pillar and has a right-angled triangular cross section, for showing the condition in which the crystalline element is used.

In the embodiment shown in FIG. 5(a), the pillar-shaped crystalline element 14d of cross section of a right-angled triangle is used. This crystalline element 14d has one incident surface 8d, one totally reflecting surface 12d, and one exit surface 13d. The condenser mirror and the objective mirror which are diagrammatically shown are disposed on axes perpendicular to each other according to the shape of the crystalline element 14d. The sample 16 is contacted with the totally reflecting surface 12d during measurement.

Figure 5B:
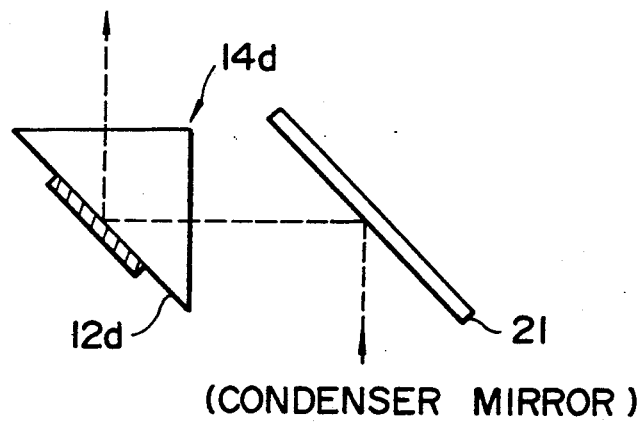

In the embodiment shown in FIG. 5(b), the pillar-shaped crystalline element 14d of right-angled triangular cross section is used. A plane mirror 21 for reflecting infrared light is disposed parallel to the totally reflecting surface 12d of this element. The plane mirror 21 is coupled to the crystalline element 14d by an adequate joining means (not shown). Therefore, this plane mirror 21 substantially corresponds to the first reflecting surface 10b of the crystalline element 14b. This embodiment is substantially identical with the embodiment described in connection with FIG. 4(b).

The physics of this embodiment is similar to that of the embodiment described already in connection with FIGS. 2 and 3 except that the infrared radiation is reflected only once or twice inside the crystalline element and that the optical axis of the reflected light is shifted from the optical axis of the incident rays. Where an area analysis is made or a line analysis is made in a given direction, the focal point deviates from the reflecting surface in the same way as in the embodiment shown in FIGS. 2 and 3. The sample stage 17 is moved to correct this deviation, and this movement makes it necessary to adjust the focus of the objective mirror 18 in the same manner as in the embodiment described previously in connection with FIGS. 2 and 3.

This embodiment yields essentially the same advantages as the embodiment of FIGS. 2 and 3. However, these embodiments have the additional advantage that infrared radiation can be guided into any desired location on the sample surface without changing the condition for total reflection, i.e., the incident angle of the infrared radiation, using a pillar-shaped crystalline element of comparatively simple cross section.

An embodiment of the above-described first aspect is next described. This embodiment includes a control system providing control of the sample stage drive mechanism, for effectively and quickly making a line analysis or area analysis. The control system is added to the drive mechanism for the sample stage 17 of the accessory for ATR IR spectroscopy to automate the adjustment of the focus of the objective mirror by the movement of the stage 17 during the line or area analysis. This control system can be similarly applied to the accessory described already in conjunction with FIG. 4 (a)-(c). This system calculates the forecasted traveling length of the crystalline element to adjust the focus of the objective mirror at a new measurement point on the totally reflecting surface when the crystalline element 14 is translated in any arbitrary direction, and operates the drive mechanism according to the results of the calculations.

In particular, we now assume that the direction of the outgoing, totally reflected light lies in the z-direction. It is also assumed that the direction of the axis of the pillar forming the crystalline element and extending perpendicularly to the z-direction lies in the y-direction and that the x-direction is perpendicular to both y- and z-directions. This control system comprises: a first calculating means for calculating the exit angular aperture of the light beam in the crystalline element from the refractive index of the pillar-shaped crystalline element and from the exit angular aperture of the light beam in air when ATR IR measurements where the point of measurement is moved and the focus is brought to the moved point of measurement are performed; a first storage means storing the angle formed between the normal to the totally reflecting surface and the optical axis of the outgoing, totally reflected light; a second storage means storing the x component of the vector drawn from the previous point of measurement prior to the movement to the new point of measurement subsequent to the movement; a second calculating means for calculating the distance to travel the crystalline element in the z-direction from the exit angular apertures in air and in the crystalline element and the reflecting angle formed between the normal to the totally reflecting surface for sample measurement and the optical axis of the outgoing rays of the totally reflected light and from the x component of the vector; and a means providing control of the operation of the sample-holding portion according to the x component of the vector and the movement in the z-direction. Note that the exit angular aperture means the angle that the light beam exiting from the crystalline element subtends relative to the objective mirror.

The control system described above can further include a third storage means storing the y component (taken in the direction along the axis of the crystalline element 14) of the vector drawn from the point of measurement prior to the movement to the point of measurement subsequent to the movement.

ATR IR measurements of the sample surface are made, using the crystalline element 14 shown in FIG. 2, by shifting the point of measurement on the x-z plane as shown in FIG. 6. The crystalline element 14 is translated in the direction indicated by the arrow 22 to shift the point of measurement on the sample 16. This changes the position at which the infrared radiation enters the crystalline element, so that the light beam 23 prior to the movement moves into the position indicated by 24 after the movement. As a result, the focal point of the condenser mirror, or the focus of the objective mirror, fails to lie on the totally reflecting surface 12. This deviation can be corrected by translating the crystalline element 14 over a requisite distance in the z-direction.

In order to correct this deviation, the first calculating means performs calculations, using the refractive index of the crystalline element and the exit angular aperture of the light beam in air, reflected by the totally reflected surface to find the exit angular aperture of the light beam in the crystalline element. The calculated angular apertures are output to the second calculating means. The first storage means stores the reflection angle formed between the normal to the totally reflecting surface for sample measurement and the optical axis of the outgoing rays of the totally reflected light. This angle is sent to the second calculating means. The second storage means stores the x component of the vector drawn from the point of measurement prior to the movement to the point of measurement subsequent to the movement. This x component is sent to the second calculating means. The second calculating means calculates the distance traveled in the z-direction needed to bring the focus of the condenser mirror, or the focus of the objective mirror, into coincidence with the point of measurement subsequent to the movement, from these three values. The computed distance is output to the control means providing control of the operation of the sample-holding portion Where the third storage means is added, this storage means stores the distance traveled in the y-direction. This distance is sent to the control means providing control of the operation of the sample-holding means.

In the present embodiment, if the focus of the condenser mirror, or the focus of the objective mirror, deviates when the point of measurement is shifted off the axis of the pillar forming the crystalline element, then the deviation can be automatically corrected by movement of the sample-holding portion. This embodiment can be carried out together with any of the embodiments described in connection with FIGS. 2 and 3 in which a line analysis is made along the axis of the pillar forming the crystalline element 14. That is, a line analysis can be made in any desired direction on the sample surface by ATR IR spectroscopy. Also, an area analysis of any desired portion on the sample surface can be easily and quickly performed by extending this kind of line analysis.

Embodiments of the third aspect are next described. The crystalline element having an engraved scale can take any shape as long as normal ATR IR measurements can be performed. Crystalline elements shaped in such a way that the optical axis of the incident rays is coincident with the optical axis of the outgoing rays are especially preferred, because point analysis, line analysis, or area analysis can be made easily and precisely with a commercially available infrared microscope. This type of crystalline element is designed so that the incident radiation is totally reflected at least once and reflected at least three times inside the element. More specifically, this crystalline element has an incident surface, at least three totally reflecting surfaces, and an exit surface. Infrared radiation coming from outside first enters the incident surface. One of the at least three reflecting surface is a totally reflecting surface. A sample is contacted with this totally reflecting surface to perform ATR IR measurements. The reflecting surfaces alter the direction of the incident radiation in such a way that the direction of the outgoing light agrees with the incident direction. The outgoing light propagating in the same direction as the incident light finally passes across the exit surface. The optical path length between the incident surface and the exit surface is so set that the incident light is focused onto the totally reflecting surface.

One example of this crystalline element is a pillar of hexagonal cross section having three pairs of parallel sides and central bent angle of 90°. A pillar of cross section of a modification of this hexagon is also available. A scale consisting of marks engraved at arbitrary intervals on one of the inner side surfaces of the pillar may be formed to fabricate a crystalline element having a scale for ATR IR spectroscopy. The engraving can be effected by scribing, etching, laser beam machining, electron beam machining, or other method. One of them is selected according to the shape of the crystalline element, the spacing between the successive marks of the scale, and the thickness of the marks.

In the above-described embodiments, the material of the reflecting crystalline element and the optical path length for the infrared radiation can be set as follows.

The reflecting surfaces of the crystalline element with which the sample under investigation is not contacted can be coated with a film of aluminum or gold to prevent decreases in the amount of the incident infrared radiation. As an example, this film can be the aforementioned processed film 11 for reflecting light. This prevents the reflectivity of the reflecting surfaces from decreasing and suppresses scattering of the infrared radiation out of the crystalline element. Consequently, the efficiency of utilization of the radiation can be enhanced.

The crystalline element can be made from materials which transmit infrared radiation and have refractive indices exceeding 2, for example, zinc selenide, thallium bromide-iodide (KRS-5), germanium, and silicon that are generally used for ATR IR measurements. To permit one to visually observe the sample surface, zinc selenide and KRS-5 which well transmit visible radiation are especially desired.

The optical path length is so set that the infrared radiation is focused onto the totally reflecting surface. This setting is accomplished at will by variously combining various factors including the material, the shape, and the size of the crystalline element, the incident and exit angular apertures, the positional relations among the crystalline element, the condenser mirror, and the objective mirror. The material of the crystalline element is determined, using its refractive index as a parameter. As an example, the crystalline element has a parallelogrammatic cross section having acute angles of 45°. The incident and exit angular apertures are both 60°. The thickness of the crystalline element taken along the optical axis is 6 mm. The refractive index is 2.4. Under these conditions, the appropriate optical path length in the crystalline element is calculated at 16.3 mm. Note that the incident angular aperture means the angle that the light beam incident on the crystalline element subtends relative to the condenser mirror Specific examples of the invention are given below.

EXAMPLE 1

In this example, a crystalline element consisting of zinc selenide was used. This element had the cross section shown in FIG. 2. An angle of 90° was made at the central bent portion. The total vertical length of the crystalline element was 6 mm. The base and the top side were 5.15 mm long The length taken along the axis of the pillar forming the element was 15 mm. This crystalline element was attached to a holder (not shown) and disposed in the optical system of an infrared microscope as shown in FIG. 3. The sample to be investigated was kept in abutment with the totally reflecting surface as shown. Under this condition, the focus of the objective mirror was brought onto this totally reflecting surface. In this optical system, the incident and exit angular apertures were 60°. The optical path length inside the crystalline element was so set that both focal point of the condenser mirror and focus of the objective mirror gathered at the same point located on the totally reflecting surface.

Figure 7:
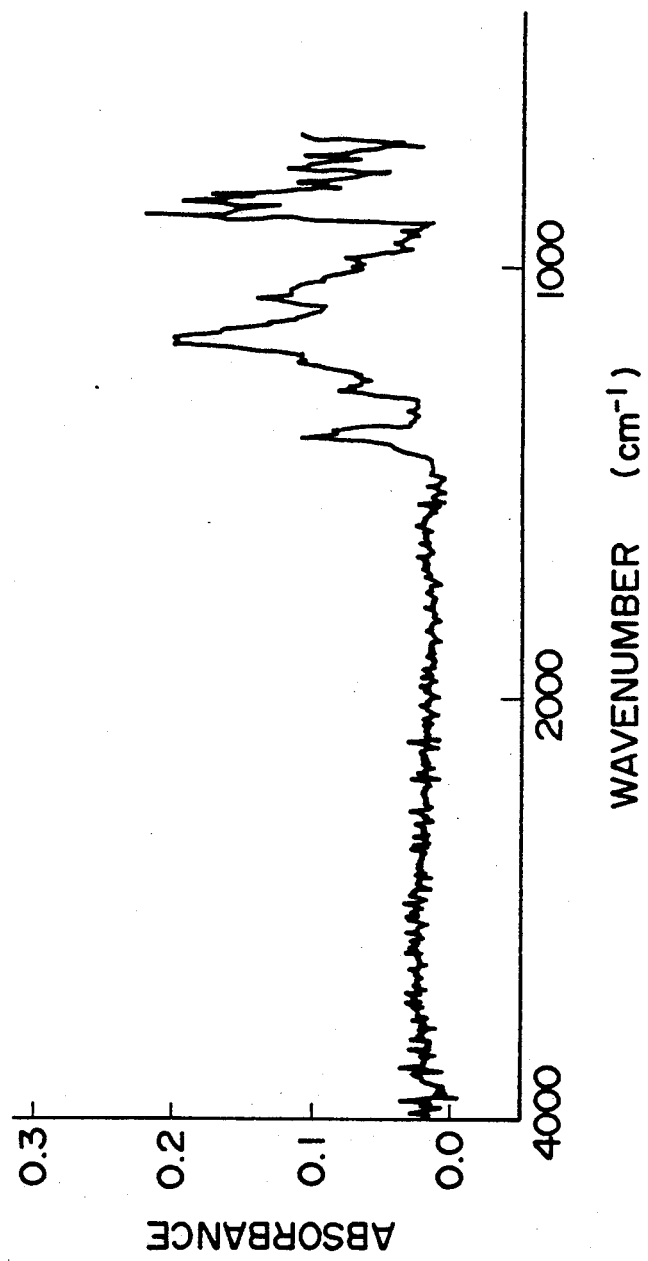
FIG. 7 is an ATR IR absorption spectrum of polyvinylidene fluoride which is in intimate contact with a crystalline element according to the invention.

A cross section of a film of polyvinylidene fluoride 12 μm thick was used as the sample to be investigated. This cross section was brought into intimate contact with the crystalline element. An ATR absorption spectrum of the infrared radiation reflecting from a field of view 10 μm square was obtained. The obtained spectrum is shown in FIG. 7. This ATR IR spectrum of the cross section 12 μm wide was clear. This demonstrates that a microscopic portion having dimensions on the order of 10 μm can be analyzed sufficiently.

EXAMPLE 2

Figure 8:
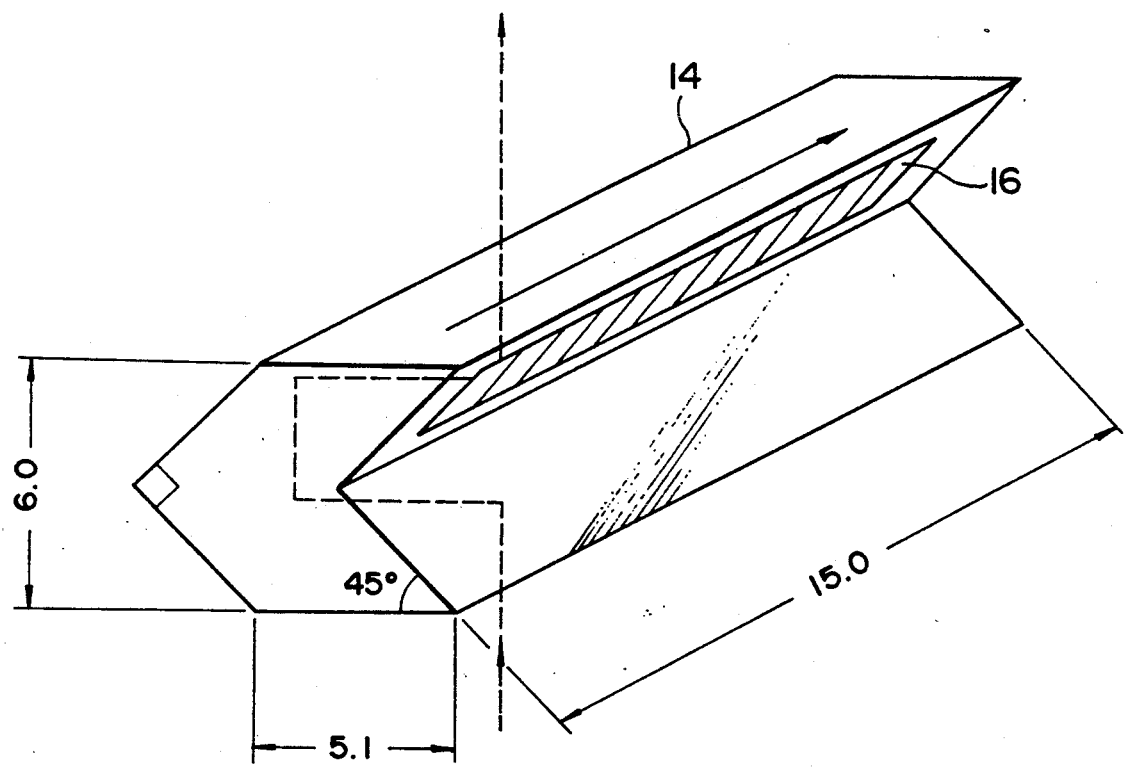
FIG. 8 is a perspective view of a crystalline element to which a composite material is contacted.
Figure 9:
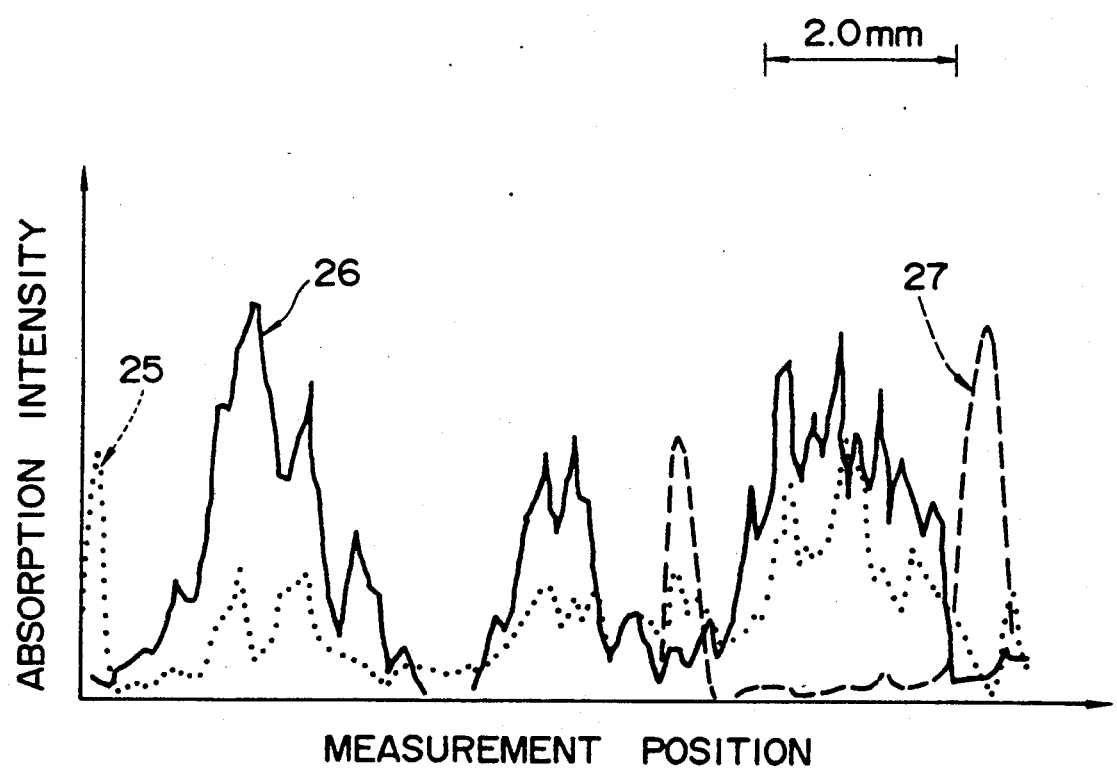
FIG. 9 is a graph showing the result obtained by a line analysis of a composite material.

As shown in FIG. 8, the same crystalline element 14 as used in Example 1 was employed. A composite material consisting of asbestos, phenolic resin, and cashew dust was used as the sample 16 to be investigated. The surface of this composite material was brought into intimate contact with the same reflecting surface of the crystalline element. A line analysis was made in the direction indicated by the arrows to obtain ATR IR absorption spectra 160 times successively. The characteristic absorption bands peculiar to the components, i.e., asbestos, phenolic resin, and cashew dust, were extracted. Their absorption intensities were plotted against the position of the point of measurement. The result is shown in FIG. 9, where the dotted line 25 indicates the absorption characteristic of phenolic resin, the solid line 26 indicates the absorption characteristic of asbestos, and the broken line 27 indicates the absorption characteristic of cashew dust. In this way, the distributions of these components on the surface of the composite material can be clearly distinguished from each other.

EXAMPLE 3

The same crystalline element as used in Example 1 was employed. Fine particles of red ink was applied to the same totally reflecting surface. The surface was visually observed with an infrared microscope. Since the observed surface was tilted at 45°, the image of the ink particles was flattened, but it could be clearly seen. Under this condition, ATR IR absorption spectra of the ink particles was derived. In this way, ATR IR absorption spectra can be obtained while observing a quite small subject by bringing the focus of the objective mirror onto the totally reflecting surface.

EXAMPLE 4

Figure 10:
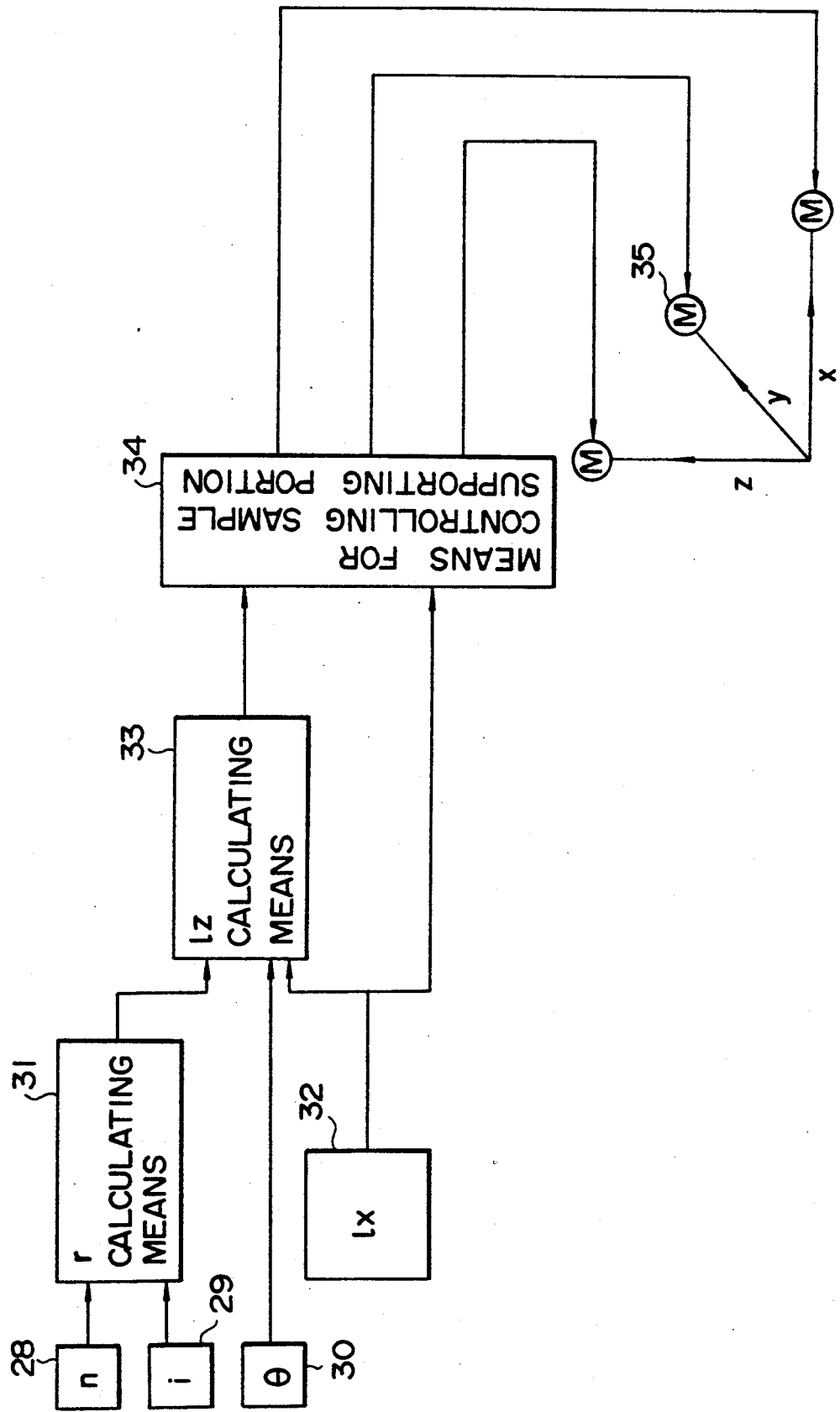
FIG. 10 is a block diagram of a control system according to the invention.

A control system shown in FIG. 10 was added to the ATR IR measurement accessory of Example 1 to control the drive mechanism, for automatically making a line analysis or area analysis. This system comprised a means 28 storing a refractive index n, a storage means 29 storing half i of the exit angular aperture in air, of the totally reflected light beam, a first storage means 30 storing the angle $\theta$ formed between the normal to the sample surface and the optical axis of the outgoing rays, a first calculating means 31 for calculating half $\gamma$ of the exit angular aperture in the crystalline element, of the totally reflected light beam, a second storage means 32 storing the distance $1_x$ traveled in the x-direction, a second calculating means 33 for calculating the distance $1_z$ traveled in the z-direction, a control means 34 receiving an input from the second storage means 32 and providing control of the sample-supporting portion, and an electric motor 35 for driving the sample-supporting portion. The x-, y-, z-directions in FIG. 10 are the same as the x-, y-, z-directions in FIG. 6.

Figure 11:
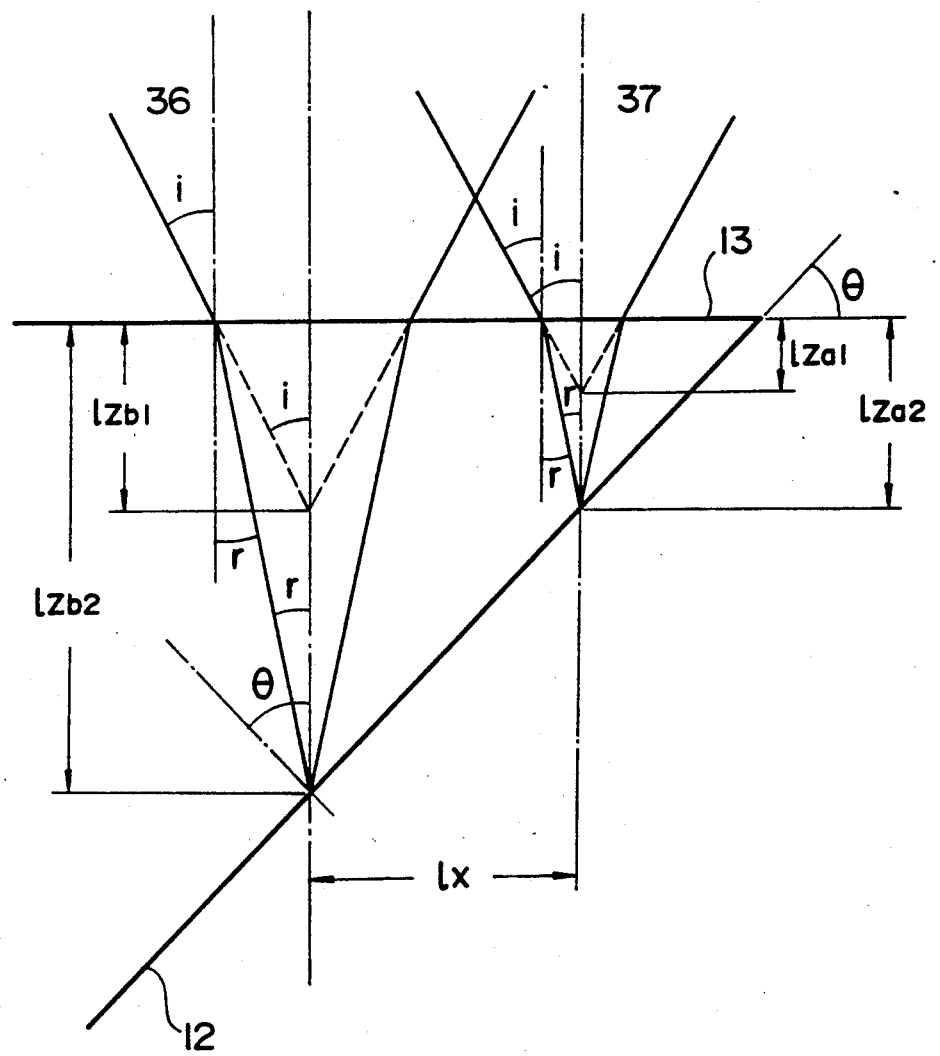
FIG. 11 is a diagram illustrating the calculations performed by the control system shown in FIG. 10.

The distance 1, traveled in the z-direction is calculated by the second calculating means 33 in the manner described now. It is assumed that the focused point of the infrared radiation and the focus of the objective mirror are located on the totally reflecting surface 12 as shown in FIG. 11. When the light beam 36 reflected toward the objective mirror prior to movement of the point of measurement is replaced by the light beam 37 reflected toward the objective mirror subsequent to the movement of the point of measurement, let $1_{zb1}$ and $1_{za1}$ be the distances from the exit surface 13 to the focus of the objective mirror through air before and after, respectively, the movement of the point of measurement. Also, let $1_{zb2}$ and $1_{za2}$ be the distances from the exit surface 13 to the focus of the objective mirror 13 through the crystalline element before and after, respectively, the movement of the point of measurement. In order to bring the focus of the objective mirror prior to the movement to the point of measurement on the totally reflecting surface 12 subsequent to the movement, it is necessary to move the sample-supporting portion over a distance of $1_{zb1} - 1_{za1} = 1_z$ in the z-direction. The relations illustrated in FIG. 11 are given by $$1_{za1} \cdot \tan i = 1_{za2} \cdot \tan \gamma \qquad (3)$$

$$1_{zb1} \cdot \tan i = 1_{zb2} \cdot \tan \gamma \qquad (4)$$

$$1_{zb2} - 1_{za2} = 1_x \cdot \tan \theta \qquad (5)$$

$$n = \sin i / \sin \gamma \qquad (6)$$

Substituting equations (3) and (4) into the traveled distance $1_z (=1_{zb1}-1_{za1})$ to be calculated results in $$1_z=(1_{zb2}-1_{za2}) \tan \gamma / \tan i$$

By substituting equation (5) into this, we have $$1_z=1_x \tan \theta \cdot \tan \gamma / \tan i$$

Since tan γ is found from equation (6) if the value of i is given, $1_z$ can be determined if the values of θ, i, n are given.

In the present example, the objective mirror whose exit angular aperture in air is 60° and the crystalline element having a refractive index of 2.4 were used. In this crystalline element, the angle made between the normal to the totally reflecting surface and the optical axis of the outgoing rays was 45°. When the distance $1_x$ traveled in the z-direction by the point of measurement was set to 100μm, the distance $1_z$ traveled in the z-direction by the point of measurement was calculated at 37 μm. The sample-supporting portion was driven according to this value, and a line analysis was made.

EXAMPLE 5

Figure 12:
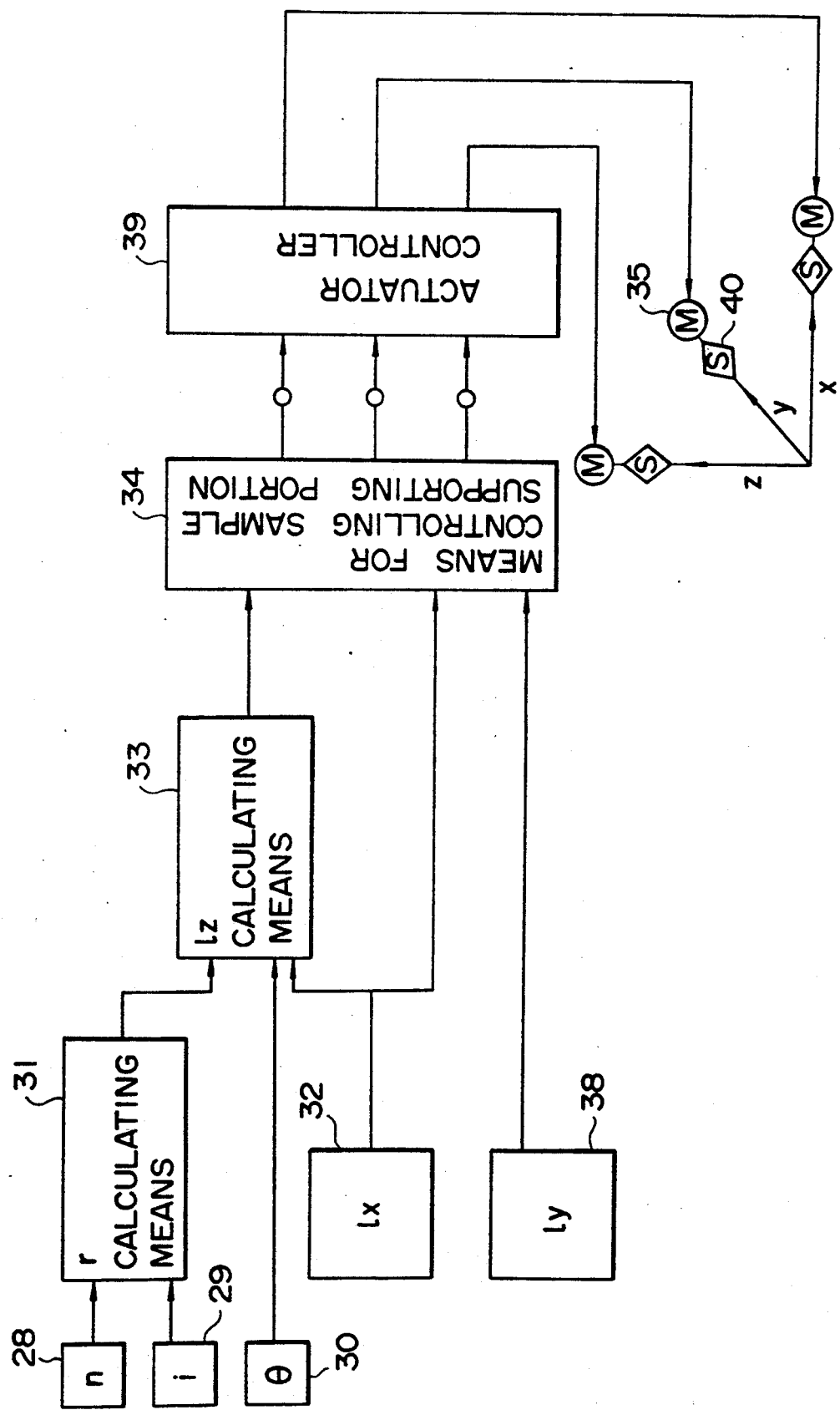
FIG. 12 is a block diagram of another control system according to the invention.

Referring to FIG. 12, a third storage means 38 storing the distance 1, traveled in the y-direction was added to the system of Example 4 described above in connection with FIG. 10. The present system enables one to make a line analysis or area analysis in any arbitrary direction. An actuator controller 39 was disposed between the control means 34 of the sample-supporting portion and the driving motor 35 of the sample-supporting portion. A position sensor 40 detecting the distance traveled was installed on the sample-supporting portion. The controller 39 could drive the driving motor 35 of the sample-supporting portion in response to the instructions given by the control means 34 of the sample-supporting portion. It is also possible to drive the motor 35 by directly entering the traveling distance to the new point of measurement. The output signal from the position sensor 40 might be fed back either to the control means 34 of the sample-supporting portion or to the actuator controller 39 to precisely move the sample-supporting portion. In the present example, an accurate automatic system can be fabricated because it is capable of automatically adjusting the objective mirror focus at any measurement point.

EXAMPLE 6

Figure 13:
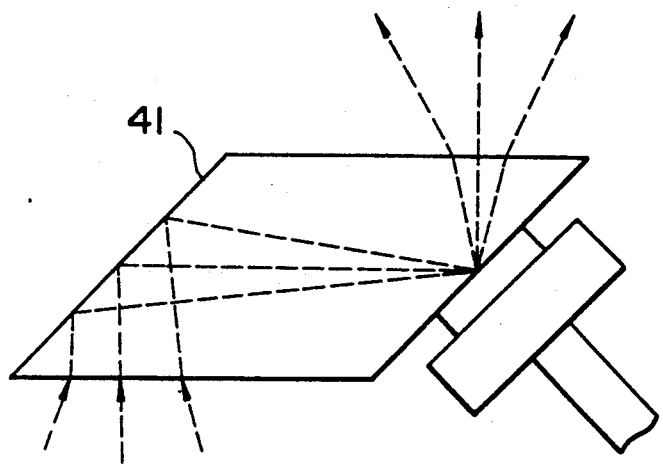
FIG. 13 is a view of a crystalline element according to the invention and associated components, for showing the condition in which the crystalline element is used.

In this example, a pillar-shaped crystalline element 41 made of zinc selenide and having a parallelogrammatic cross section as shown in FIG. 13 was used. This cross section had acute angles of 45°. The total vertical length of the crystalline element was 6 mm. The bottom and the top sides were 10.3 mm long. The length of the crystalline element taken along the axis of the pillar was 15 mm. This crystalline element was attached to a holder (not shown) and disposed in the optical system (not shown) of an infrared microscope in the same way as in the example illustrated in conjunction with FIG. 3. The optical axis of the condenser mirror was spaced 10.3 mm from the optical axis of the objective mirror. The focus of the objective mirror was brought onto the totally reflecting surface. In this optical system, the incident angular aperture and the exit angular aperture were both 60°. The focal point of the condenser mirror and the focus of the objective mirror gathered at a same point positioned o the totally reflecting surface.

Figure 14:
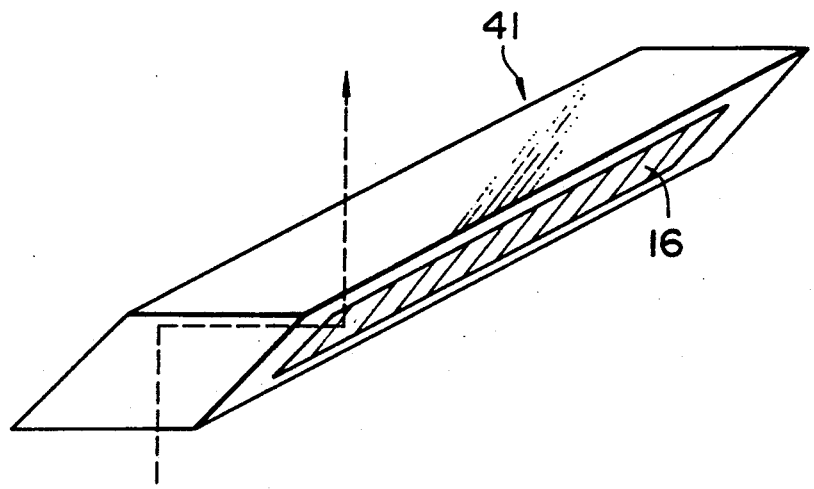
FIG. 14 is a perspective view of a crystalline element to which red ink has been applied, the crystalline element being used as a sample to be investigated.
Figure 15:
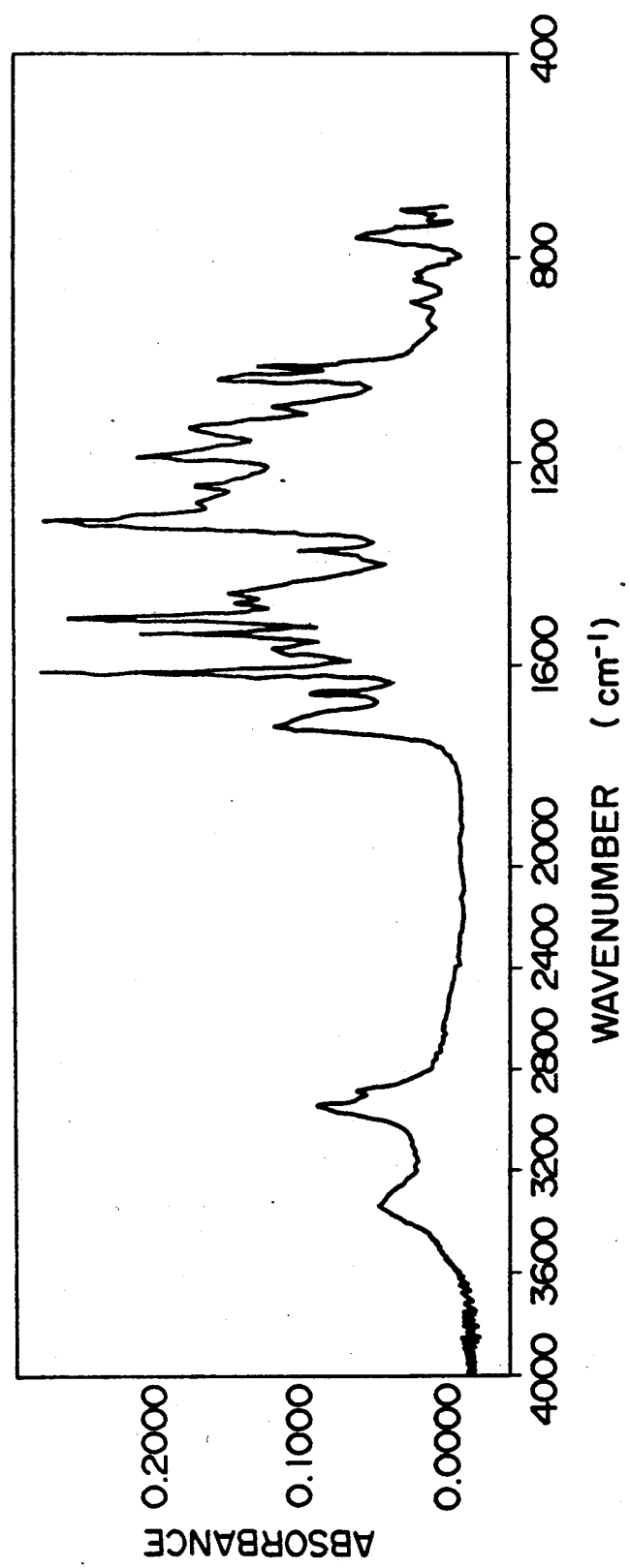
FIG. 15 is an ATR IR absorption spectrum of a fine particle of the red ink shown in FIG. 14.

Red ink containing fine particles having a diameter of 50 μm were applied as the above-described sample 16 to the whole of the totally reflecting surface of the crystalline element 41 as shown in FIG. 14. The infrared radiation reflected from the fine particle within a field of view 10 μm square was restricted by a slit, and then the radiation was directed to a detector. In this way, an ATR IR absorption spectrum was obtained. This spectrum is shown in FIG. 15. It can be seen that the derived spectrum is clear and that a microscopic portion having dimensions on the order of 10 μm can be analyzed sufficiently.

EXAMPLE 7

Figure 16A:
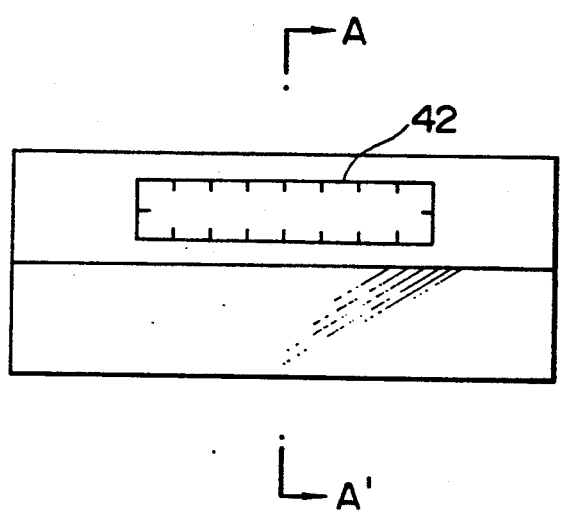
FIG. 16(A) is a view showing the totally reflecting surface formed in the crystalline element used in Example 1, the surface having a scale.
Figure 16B:
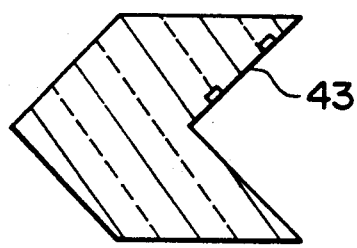
FIG. 16(B) is a cross-sectional view taken on line A—A' of FIG. 16(A)

The shape of the crystalline element of zinc selenide used in the present example is shown in FIG. 16. The sample was contacted with the totally reflecting surface 43 as shown in FIG. 16(B). A scale 42 forming two dimensional coordinates for identifying the location of a point of measurement was engraved on this surface as shown in FIG. 16(A). The patterns of the scale are indicated by numerals 44 and 45 in FIGS. 17 and 18, respectively. The pattern 44 of FIG. 17 was adapted for a local analysis. The pattern of FIG. 18 was adapted for a line analysis or area analysis. The pattern 45 of FIG. 18 was created in such a way that the scale would not impede the measurement when a line or area analysis was made. An ATR IR measurement of acrylic resin which hardly absorbs visible light was attempted, using this crystalline element.

As a comparative example, a crystalline element which was similar to the present example of crystalline element except that no scale was formed on it was used. Visible light was introduced as totally reflected light, and observation of the sample was attempted. This observation was impossible to achieve.

Figure 17:
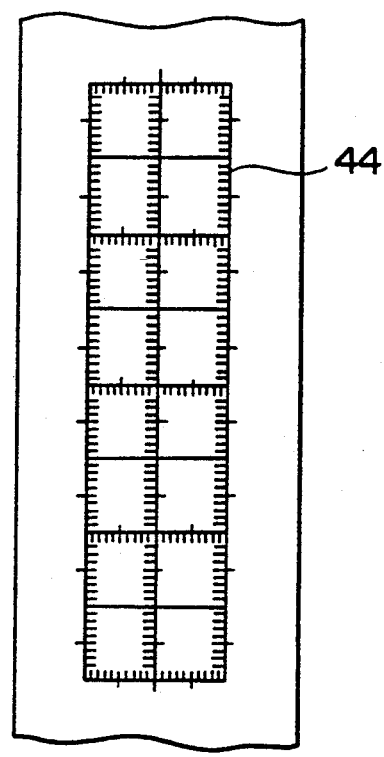
FIG. 17 is a view showing the pattern of a scale used for a point analysis in this embodiment.

The sample of acrylic resin was contacted with the totally reflecting surface of the present example of crystalline element, the surface having the scale of the pattern shown in FIG. 17. The sample was observed under an optical microscope. At this time, both sample and scale engraved on the crystalline element were observed. The point located at the tenth vertical mark and at the tenth horizontal mark was subjected to a point analysis. The crystalline element was transported to the microscope for ATR IR measurements while the sample was maintained in abutment with the element. Visible light was introduced as totally reflected light, and the focus was adjusted by positioning the sample-supporting portion. It was found that only the scale on the crystalline element surface could be confirmed. This focus was brought to the position indicated by the tenth vertical mark and the tenth horizontal mark. The vertical direction was taken along the axis of the pillar-shaped crystalline element. Then, infrared radiation was introduced to obtain ATR IR absorption spectra, for the point analysis. A crystalline element having exactly the same shape and having the scale pattern shown in FIG. 18 was employed. The infrared radiation was focused to the position indicated by the tenth vertical mark and the tenth horizontal mark and an ATR IR absorption spectrum was derived in exactly the same way as in the above-described process. Then, a spectrum was obtained similarly from a position indicated by the eleventh vertical mark and the tenth horizontal mark. This operation was repeated with successively increasing or shifted vertical mark while maintaining the horizontal position at the tenth mark. Thus, a line analysis of the sample was made. In consequence, spectra were derived from a line having a length of 1 mm.

EXAMPLE 8

Figure 19A:
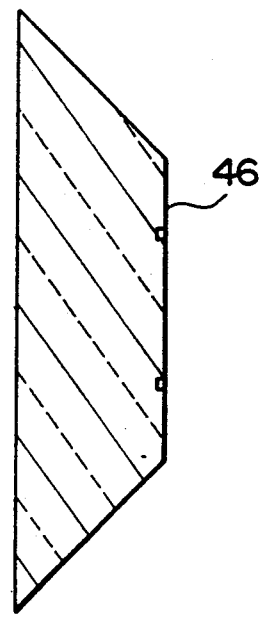
FIG. 19(A) is a cross-sectional view taken on line A—A' of FIG. 19(B)
Figure 19B:
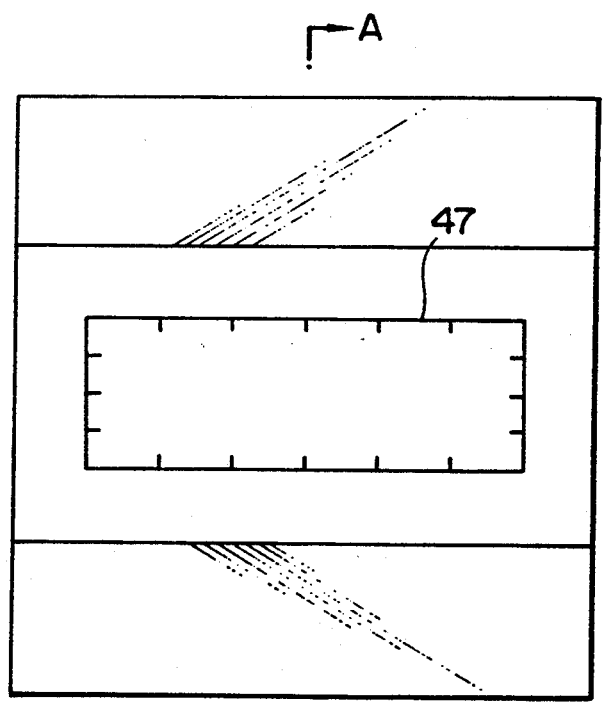
FIG. 19(B) is a view showing the totally reflecting surface formed on the crystalline element used in Example 2, the surface having a scale.

A scale in the pattern 47 shown in FIG. 17 was engraved on the totally reflecting surface 46 of a crystalline element of zinc selenide. This crystalline element was of trapezoidal cross section as shown in FIG. 19. A point analysis was made in a manner similar to the measurement of Example 7 except that an infrared microscope where the optical axis of the incident rays was at right angles to the optical axis of the objective mirror was employed. In this way, ATR IR spectra were obtained from a microscopic portion.

EXAMPLE 9

Figure 18:
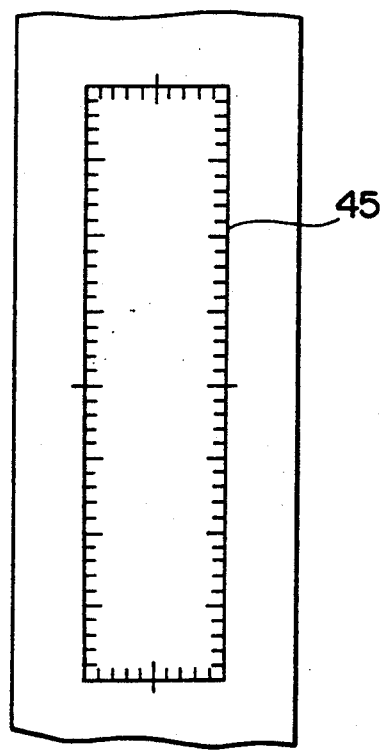
FIG. 18 is a view showing the pattern of a scale used for a line analysis.
Figure 20A:
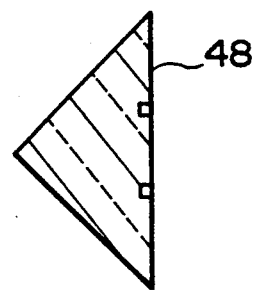
FIG. 20(A) is a cross-sectional view taken on line A—A' of FIG. 20(B)
Figure 20B:
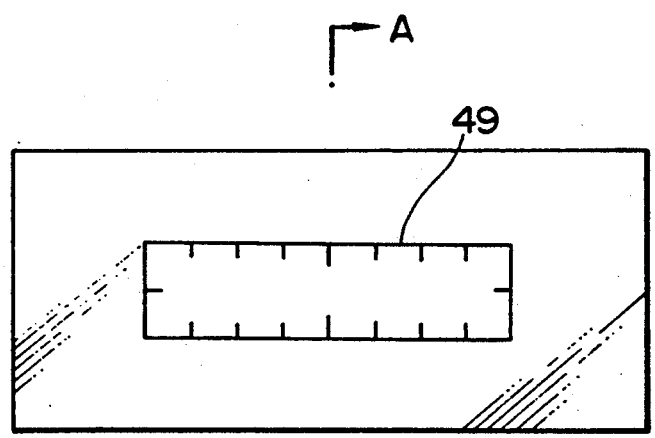
FIG. 20(B) is a view showing the totally reflecting surface formed on the crystalline element used in Example 3, the surface having a scale.

A scale in the pattern 49 shown in FIG. 18 was engraved on the totally reflecting surface 48 of a pillar-shaped crystalline element of zinc selenide. This element was of triangular cross section as shown in FIG. 20. A line analysis was made in a manner similar to the measurement of Example 7 except that an infrared microscope where the optical axis of the incident rays was at right angles to the optical axis of the objective mirror was employed.

What is claimed is:

1. An accessory for attenuated total reflection (ATR) infrared (IR) spectroscopy, comprising:
   a condenser mirror for converging infrared radiation;
   a supporting portion for holding a crystalline element and a sample to be investigated;
   said crystalline element comprising an incident surface on which infrared radiation from the condenser mirror falls, a totally reflecting surface with which the sample is contacted and which permits a single total reflection of the infrared radiation, and an exit surface through which outgoing rays of the infrared radiation finally exit from the crystalline element;
   means for selectively passing the infrared radiation exiting from the exit surface; and
   an objective mirror which is disposed opposite to the exit surface of the crystalline element and which can be focused to the point of measurement of the sample contacted with the totally reflecting surface, the optical path length of the accessory being so set that the converged point of the infrared radiation lies on the totally reflecting surface of the crystalline element,
   wherein said crystalline element is a pillar whose incident surface, totally reflecting surface, and exit surface are plane surfaces parallel to the axis of the pillar and the axis of which extends at right angles to the optical axis of the outgoing rays, and wherein said supporting portion has a drive mechanism capable of translating the crystalline element at least along the axis of the pillar.

2. The accessory of claim 1, wherein said crystalline element comprising:
   at least three reflecting surfaces including said totally reflecting surface and acting to alter the direction of the incident radiation;
   the reflecting surfaces being so oriented that the optical axis of the incident radiation agrees with the optical axis of the outgoing radiation.

3. The accessory of claim 1, wherein said totally reflecting surface with which the sample undergoing ATR IR measurements is contacted has at least one scale engraved on this surface deeper than the surface roughness of this totally reflecting surface.

4. A crystalline element placed on a supporting portion of an accessory for ATR IR spectroscopy, the supporting portion holding a sample to be investigated, the crystalline element comprising:
   an incident surface on which infrared radiation coming from a condenser mirror falls;
   a totally reflecting surface with which the sample is contacted and which totally reflects the infrared radiation only once;
   at least three reflecting surfaces including said totally reflecting surface and acting to alter the direction of the incident radiation; and
   an exit surface through which the infrared radiation finally exits from the crystalline element, wherein said crystalline element is of a pillar shape having a cross section perpendicular to the pillar axis of the in which the ratio of the width of the incident surface versus the length between the incident surface and the exit surface is not less than $\frac{1}{2}$, and said at least three reflecting radiation agrees with the optical axis of the outgoing radiation.

5. The crystalline element of claim 4, wherein said pillar is of pentagonal cross section having one corner recessed inward.

6. The crystalline element of claim 4, wherein said pillar is of hexagonal cross section having one corner recessed inward.

7. An accessory for attenuated total reflection infrared spectroscopy and capable of performing an area analysis, comprising:
   a bipolar light source for radiating either visible radiation or infrared radiation by switching arbitrarily;
   a condenser mirror for conveying radiation from the bipolar light source onto a point of measurement of the surface of a sample to be investigated;
   a supporting portion for holding a crystalline element and the sample and movable in at least two dimensions to enable the area analysis;
   said crystalline element being a pillar comprising an incident surface on which radiation from the condenser mirror falls, a totally reflecting surface with which the sample is connected and which permits a single total reflection of the radiation and an exit surface through which the radiation finally exits from the crystalline element, the optical path length thereof being so set that a converged point of the radiation lies on the totally reflecting surface;
   an objective mirror which is disposed opposite to the exit surface of the crystalline element and which can be focused to the point of measurement on the sample; and
   a slit for selectively passing the radiation exiting from the exit surface,
   thereby determining a location of the point of measurement on the sample by visually observing the sample with visual radiation through the objective mirror and thereafter carrying out ATR IR measurement by changing the light surface from visual radiation to infrared radiation.

8. The accessory of claim 7, wherein
   said crystalline element further comprises at least three reflecting surfaces including said totally reflecting surface and acting to alter the direction of the incident radiation, and has a cross section perpendicular to the axis of the pillar in which the ratio of the width of the incident surface versus the length between the incident surface and the exit surface is not less than ½, and said at least three reflecting surfaces are so oriented that the optical axis of the incident radiation agrees with the optical axis of the outgoing radiation.

9. An accessory for attenuated total reflection (ATR) infrared (IR) spectroscopy, comprising:
   a condenser mirror for converging infrared radiation;
   a supporting portion for holding a crystalline element and a sample to be investigated;
   said crystalline element comprising an incident surface on which infrared radiation from the condenser mirror falls, a totally reflecting surface with which the sample is contacted and which permits a single total reflection of the infrared radiation, and an exit surface through which outgoing rays of the infrared radiation finally exit from the crystalline element;
   means for selectively passing the infrared radiation exiting from the exit surface; and
   an objective mirror which is disposed opposite to the exit surface of the crystalline element and which can be focused to a point of measurement of the sample contacted with the totally reflecting surface, the optical path length of the accessory being so set that the converged point of the infrared radiation lies on the totally reflecting surface of the crystalline element,
   wherein said crystalline element is a pillar whose incident surface, totally reflecting surface, and exit surface are plane surfaces parallel to the axis of the pillar and the axis of which extends at right angles to the optical axis of the outgoing rays, and wherein said supporting portion has a drive mechanism capable of translating the crystalline element at will in three dimensions, the drive mechanism comprising a calculating means for calculating the amount of movement made along the axis of the outgoing rays to adjust the focal point of said object mirror to the measurement point on the totally reflecting surface when the crystalline element is translated not parallel to the axis of the pillar, and a control means for operating the drive mechanism according to the results of these calculations.

10. The accessory of claim 9, wherein said control means comprises:
    a calculating means for calculating half of the exit angular aperture of the infrared radiation in the crystalline element from the refractive index of the pillar-shaped crystalline element and from the exit angular aperture of the infrared radiation in air;
    a first storage means storing the angle formed between the normal to the totally reflecting surface of the crystalline element and the optical axis of the outgoing rays in the totally reflecting surface;
    a second storage means storing a component of vector drawn from the point of measurement prior to movement to the point of measurement subsequent to the movement, said component orienting to x-direction which is perpendicular to z-direction, the optical axis of the outgoing rays of the totally reflected light, and also to y-direction, the axis of the pillar forming the crystalline element;
    a second calculating means for calculating the distance at which the crystalline element travels in the z-direction from the exit angular apertures in air and in the crystalline element, and from said component of the vector taken in the x-direction; and
    a means providing control of the operation of the supporting portion according to the x and z components of the vector.

11. The accessory of claim 10, wherein said control means further includes a third storage means storing the y component of the vector drawn from the point of measurement prior to the movement to the point of measurement subsequent to the movement.

12. The accessory of claim 9, wherein said crystalline element comprising:
    at least three reflecting surfaces including said totally reflecting surface and acting to alter the direction of the incident radiation;
    the reflecting surfaces being so oriented that the optical axis of the incident radiation agrees with the optical axis of the outgoing radiation.

13. The accessory of claim 9, wherein said totally reflecting surface with which the sample undergoing ATR IR measurements is contacted has at least one scale engraved on this surface deeper than the surface roughness of this totally reflecting surface.

14. An accessory for attenuated total reflection (ATR) infrared (IR) spectroscopy, comprising:
    a condenser mirror for converging infrared radiation;
    a supporting portion for holding a crystalline element and a sample to be investigated;
    said crystalline element comprising an incident surface on which infrared radiation from the condenser mirror falls, a totally reflecting surface with which the sample is contacted and which permits a single total reflection of the infrared radiation, and an exit surface through which outgoing rays of the infrared radiation finally exit from the crystalline element;
    means for selectively passing the infrared radiation exiting from the exit surface;
    an objective mirror which is disposed opposite to the exit surface of the crystalline element and which can be focused to a point of measurement of the sample contacted with the totally reflecting surface, the optical path length of the accessory being so set that the converged point of the infrared radiation lies on the totally reflecting surface of the crystalline element; and
    wherein said totally reflecting surface with which said sample undergoing ATR IR measurements is contacted has at least one scale engraved on this surface deeper than the surface roughness of this totally reflecting surface.

15. A crystalline element having a totally reflecting surface with which a sample undergoing ATR IR measurements is contacted and having at least two scale lines which form two dimensional coordinates for identifying the location of a point of measurement on the sample, engraved on the total reflecting surface deeper than the surface roughness of the totally reflecting surface.

16. A crystalline element having a totally reflecting surface with which a sample undergoing ATR IR measurements is contacted and having at least one scale engraved on said totally reflecting surface deeper than the surface roughness of the totally reflecting surface, wherein said crystalline element is a pillar of pentagonal cross section having one corner recessed inward.

17. A crystalline element having a totally reflecting surface with which a sample undergoing ATR IR measurements is contacted and having at least one scale engraved on said totally reflecting surface deeper than the surface roughness of the totally reflecting surface,
   wherein said crystalline element is a pillar of hexagonal cross section having one corner recessed inward.

* * * * *

UNITED STATES PATENT AND TRADEMARK OFFICE
CERTIFICATE OF CORRECTION

PATENT NO. : 5,216,244
DATED : June 1, 1993
INVENTOR(S) : Yasuo Esaki et al.

It is certified that error appears in the above-indentified patent and that said Letters Patent is hereby corrected as shown below:

On the title page, Item [30],

The Fourth Foreign Application Priority Data has been omitted, should read: --Jun. 20, 1991 [JP] Japan..............3-177117--

Signed and Sealed this

Eighteenth Day of January, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,216,244
DATED : June 1, 1993
INVENTOR(S) : Yasuo ESAKI, ET AL

It is certified that error appears in the above-indentified patent and that said Letters Patent is hereby corrected as shown below:

Column 20, claim 4, lines 21 and 22, change, "the pillar axis of the in which" to --the axis of the pillar in which-- line 25, after "reflecting" insert
-- surfaces are so oriented that the optical axis of the incident--.

Col. 20, claim 7, line 39, change "measurement of" to --measurement on--.

Column 21, claim 9, lines 44 and 45, change "object" to -- objective--.

Signed and Sealed this

Twelfth Day of April, 1994

Attest:

BRUCE LEHMAN

Attesting Officer

Commissioner of Patents and Trademarks